United States Patent
Burghardt et al.

(10) Patent No.: US 8,026,345 B2
(45) Date of Patent: Sep. 27, 2011

(54) CHARACTERIZATION AND IDENTIFICATION OF UNIQUE HUMAN ADIPONECTIN ISOFORMS AND ANTIBODIES

(75) Inventors: Charles Roger Burghardt, Mahwah, NJ (US); Jarema Peter Kochan, Towaco, NJ (US); Erik Roy Rasmussen, Holbrook, NY (US)

(73) Assignee: Hoffmann-La Roche Inc., Nutley, NJ (US)

( * ) Notice: Subject to any disclaimer, the term of this patent is extended or adjusted under 35 U.S.C. 154(b) by 270 days.

(21) Appl. No.: 11/968,295

(22) Filed: Jan. 2, 2008

(65) Prior Publication Data

US 2009/0123943 A1     May 14, 2009

Related U.S. Application Data

(60) Provisional application No. 60/879,179, filed on Jan. 8, 2007.

(51) Int. Cl.
*C07K 16/00* (2006.01)
*A61K 39/00* (2006.01)
*A61K 39/395* (2006.01)

(52) U.S. Cl. ............ 530/388.25; 424/139.1; 424/141.1; 424/145.1; 424/158.1

(58) Field of Classification Search .................. None
See application file for complete search history.

(56) References Cited

FOREIGN PATENT DOCUMENTS

| WO | WO 03/055916 | 7/2003 |
|---|---|---|
| WO | WO 2004/022596 | 3/2004 |
| WO | WO 2005/094200 | 10/2005 |

OTHER PUBLICATIONS

Information Hyperlinked Over Proteins (iHOP), entry for ADIPQQ, retrieved from http://www.ihop-net.org/UniPub/iHOP/gs/94596.html on Jun. 20, 2010 (one page).*
Janeway et al., Immunobiology, 3rd Edition (1997), Garland Press, pp. 3:7-3:11.*
Neumeier, M. et al, *Jour of Leukocyte Bio*, vol. 79, (2006) 803-808.
Peake, P. et al, *Euro. Jour. of Endocrinology*, (2005) 153 409-417.
Ujiie, H. et al, *Jour. of Cellular Biochem*, 98(1), 194-207 (2006).
Arita, Y. et al, *Biochem and Biophys Res. Comm.*, 257(1) 79-83 (1999).
Davies, J. et al, *Immunotech*, 2(3), 169-179 (1996).
Holt, L. et al, *Trends in Biotech*, 21(11) 484-490 (2003).
Little, M et al, *Immunology Today* 21(8), 364-370 (2000).

* cited by examiner

*Primary Examiner* — Gail R Gabel
*Assistant Examiner* — Christine Foster
(74) *Attorney, Agent, or Firm* — George W. Johnston; Dennis P. Tramaloni

(57) ABSTRACT

The invention pertains to methods for measuring different forms of human adiponectin that are present in human plasma/serum, and more specifically methods are based on an ELISA assay that utilizes different monoclonal antibodies directed against adiponectin, in combination with different polyclonal antibodies directed against different domains of human adiponectin. The invention also provides unique isoforms of adiponectin and antibodies thereto, including polyclonal and monoclonal antibodies.

2 Claims, 59 Drawing Sheets

Figure 1

Human Adiponectin Amino Acid Sequence

Start of mature protein ↓

1   MLLLGAVLLLLALPGHDQETTTQGPGVLLPLPKGACTGWMAGIPGHPGHNGAPGRDG   57

58  RDGTPGEKGEKGDPGLIGPKGDIGETGVPGAEGPRGFPGIQGRKGEPGEGAYVYRSAFSV  117

118 GLETYVTIPNMPIRFTKIFYNQQNHYDGSTGKFHCNIPGLYYFAYHITVYMKDVKVSLFK  177

178 KDKAMLFTYDQYQENNVDQASGSVLLHLEVGDQVWLQVYGEGERNGLYADNDNDSTFTGF  237
                                                    ↑
238 LLYHDTN  244                              N-linked glycosylation site Encompass all common and uncommon polymorphisms for adiponectin

Figure 2

Adiponectin Molecular Forms

Monomer        Hexamer

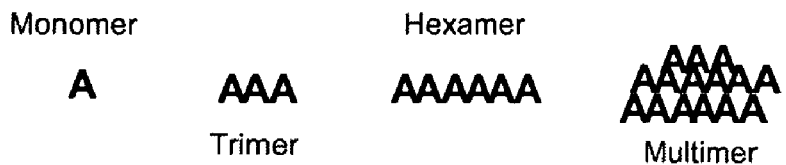

Trimer        Multimer

Molecular forms are monomers, trimers, hexamers, and various higher order multiples of adiponectin Any of these adiponectin forms can consist of different post-translational variations in any one or more adiponectin subunit, consisting of protease cleavage, glycosylation, acylation, amidation, ribosylation, etc

Adiponectin Polyclonal Abs

Antibodies

N-ter - etttqgpgvllplpkgastgc   monoclonal & polyclonal Abs

C-ter - cyadndn dstftgfllyhdtn   polyclonal Abs gACRP30 – aa 107 - 244   polyclonal Abs Commercial mAbs are directed to various sites on the adiponectin protein. The exact position is not known.

Adiponectin ELISA Assay

Specific Adiponectin Isoform ELISA Assay

Polyclonal antibody directed to specific adiponectin epitope

Monoclonal antibody directed to specific adiponectin epitope

Only a specific adiponectin isoform is detected, based on the combination of a unique polyclonal and monoclonal antibody which is used in the ELISA assay Standards curve with MAB3604 monoclonal antibody
globular domain x-axis = adiponectin concentration (ng)

Standards curve with MAB3604 monoclonal antibody

N-terminal domain x-axis = adiponectin concentration (ng)

Standard curve with A12820 monoclonal antibody globular domain x-axis = adiponectin concentration (ng)

x-axis = adiponectin concentration (ng)

Standard curve with A12820 monoclonal antibody

C-terminal domain x-axis = adiponectin concentration (ng)

Standard curve with MAB10651 monoclonal antibody globular domain x-axis = adiponectin concentration (ng)

Standard curve with MAB10651 monoclonal antibody

N-terminal domain x-axis = adiponectin concentration (ng)

Standard curve with MAB10651 monoclonal antibody

C-terminal domain x-axis = adiponectin concentration (ng

Standard curve with N-ADIP-M1 monoclonal antibody
globular domain x-axis=adiponectin concentration (ng)

Standard curve with N-ADIP-M1 monoclonal antibody

N-terminal domain x-axis=adiponectin concentration (ng)

Standard curve with N-ADIP-M1 monoclonal antibody

C-terminal domain x-axis=adiponectin concentration (ng)

Standard curve with N-ADIP-M24 monoclonal antibody
globular domain x-axis= adiponectin concentration (ng)

Standard curve with N-ADIP-M24 monoclonal antibody

N-terminal domain x-axis= adiponectin concentration (ng)

Standard curve with N-ADIP-M24 monoclonal antibody

C-terminal domain x-axis= adiponectin concentration (ng)

Figure 12 - Replacement
Standard curve with R&D Systems adiponectin assay
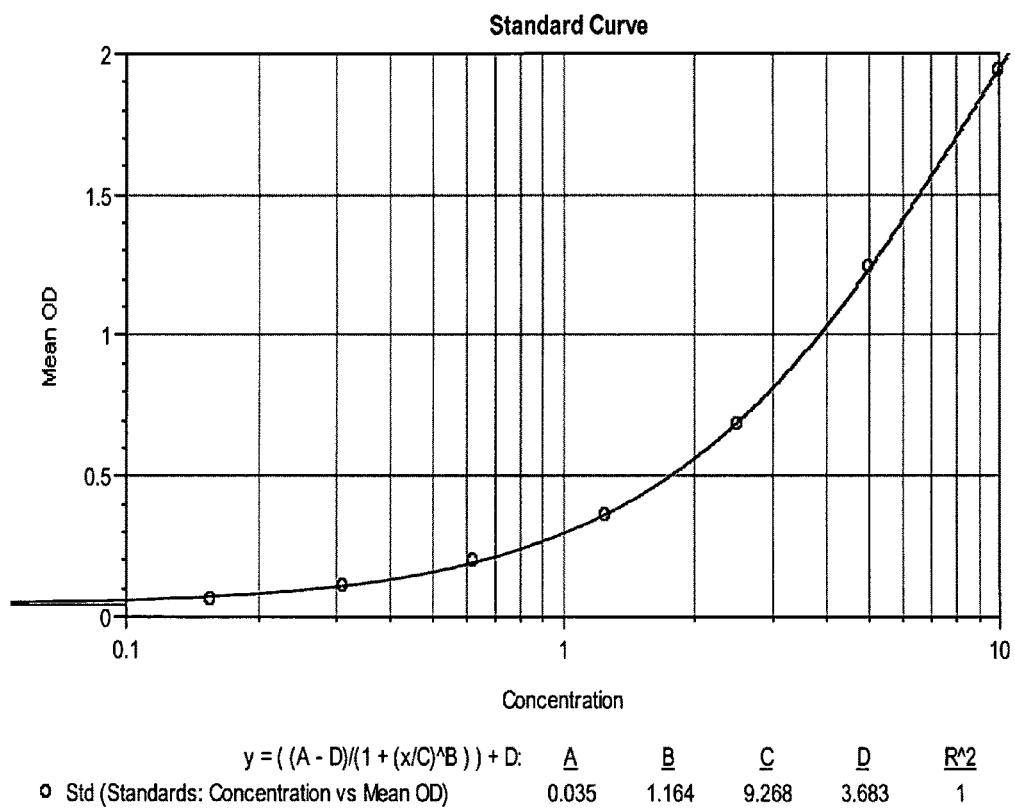
x-axis= adiponectin contration (ng)

Figure 13 - Replacement
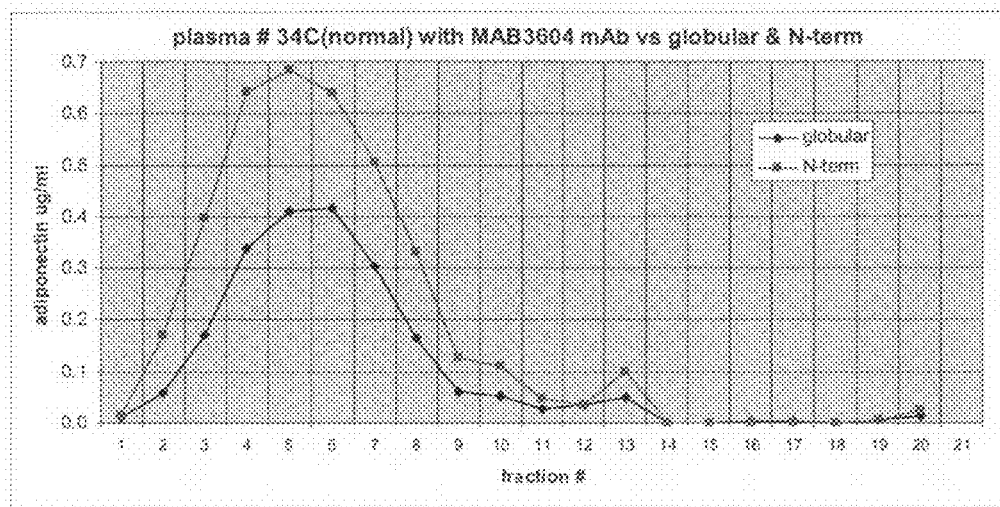
Figure 14 - Replacement
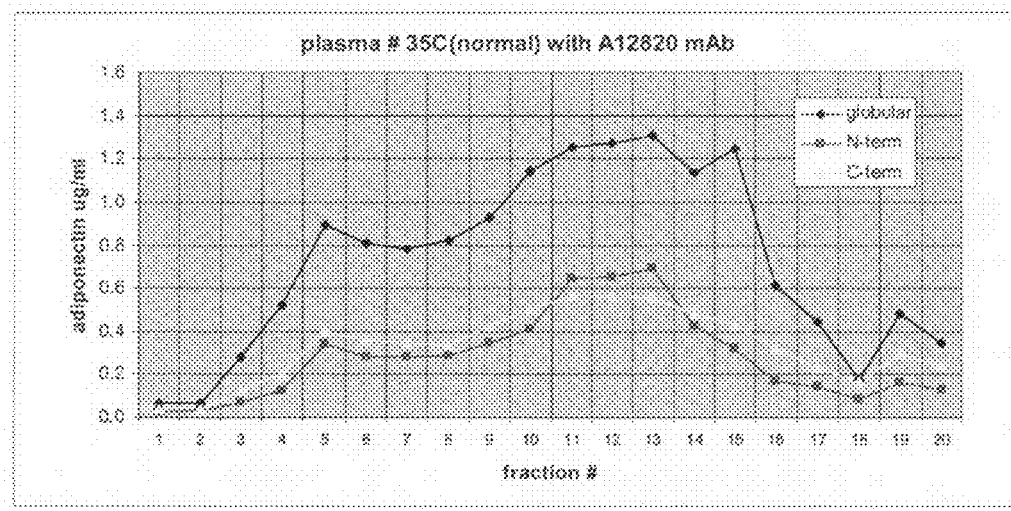

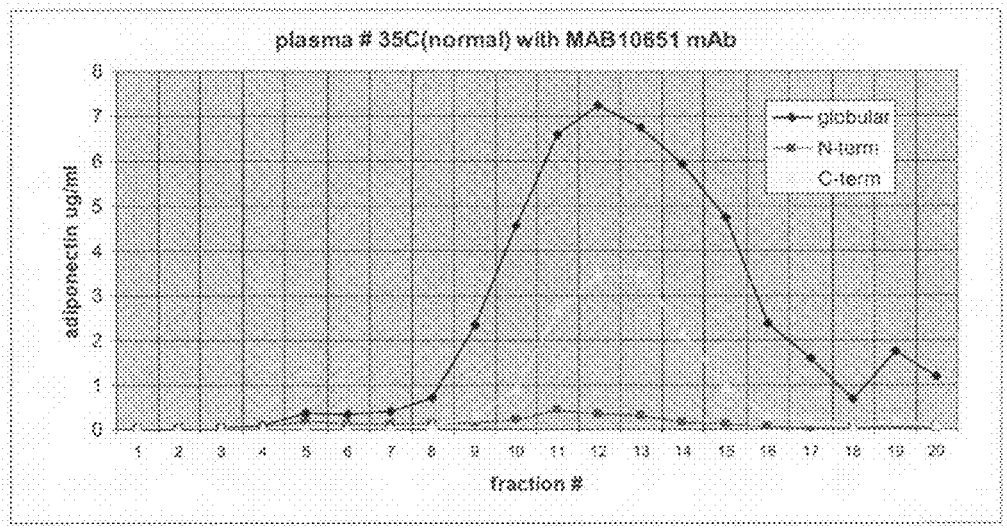
Figure 15 - Replacement
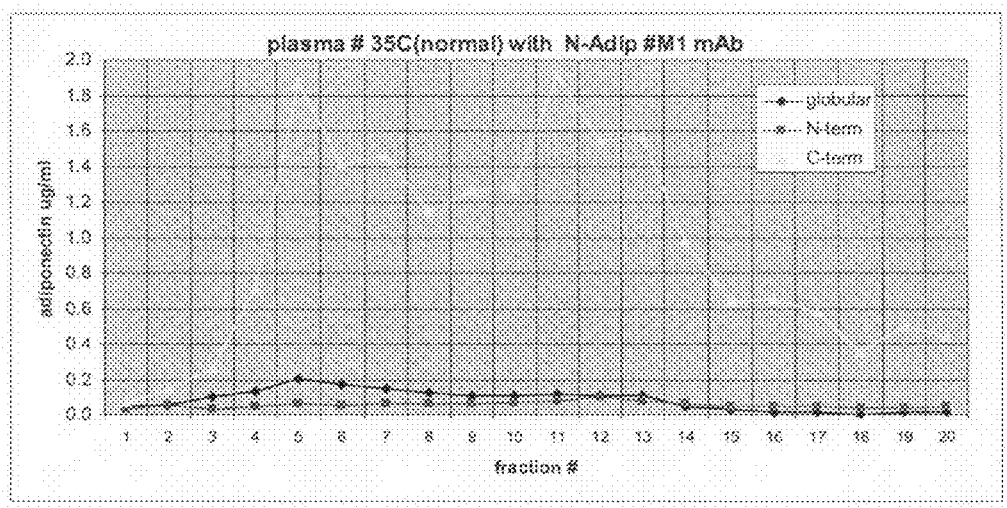
Figure 16

Figure 17 - Replacement
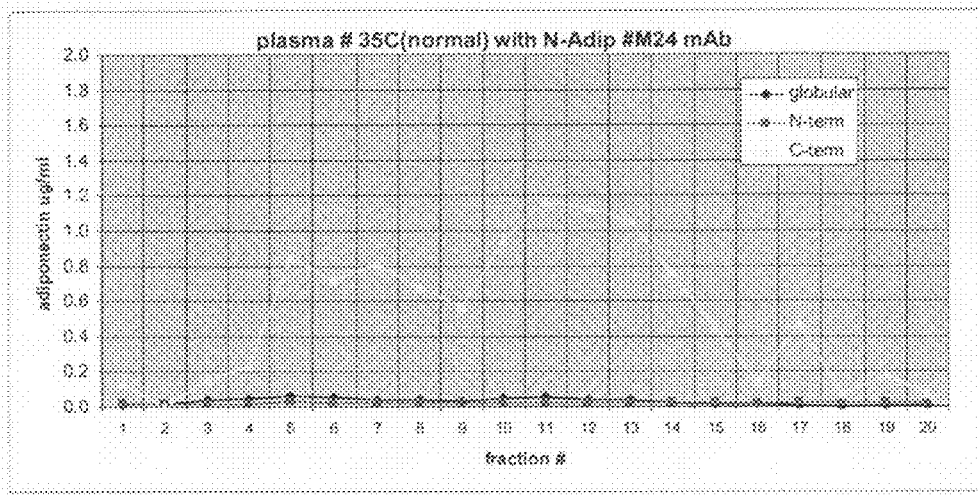
Figure 18 - Replacement
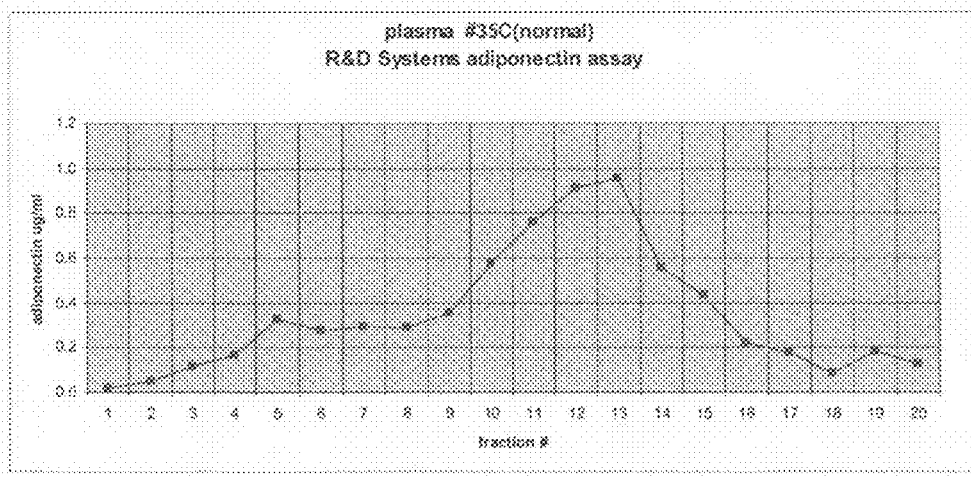

Figure 32A

M 1 Light Chain Variable Region

Nucleotide Sequence
```
ATGACCCAGA CTCCACTCTC CCTGCCTGTC AGTCTTGGAG ATCAAGCCTC

CATCTCTTGC AGATCTAGTC AGAGTATTGT ATATAGTAAT GGAAACACCT

ATTTAGAATG GTACCTGCAG AAACCAGGCC AGTCTCCAAA GCTCCTGATC

TACAAAGTTT CCAACCGATT TTCTGGGGTC CCAGACAGGT TCAGTGGCAG

TGGATCAGGG ACAGATTTCA CACTCAAGAT CAGCAGAGTG GAGGCTGAGG

ATCTGGGAGT TTATTACTGC TTTCAAGGTT CGCATGTTCG TCGGACGTTC

GGTGGAGGCA CCAAGCTGGA AATCAGACG
```

Amino Acid Sequence
```
MTQTPLSLPV SLGDQASISC RSSQSIVYSN GNTYLEWYLQ KPGQSPKLLI

YKVSNRFSGV PDRFSGSGSG TDFTLKISRV EAEDLGVYYC FQGSHVRRTF

GGGTKLEIRR
```

Figure 32B

M 1 Heavy Variable Region

Nucleotide Sequence
```
AGCTGGTGGA GATCATGGGC TGATCTTGTG AGGCCAGGGG CCTTAGTCAA

GTTGTCCTGC AAAGCTTCTG GCTTCAACAT TAAAGACTTC CATATGAGTT

GGGTGAAGCA GAGGCCTGAA CAGGGCCTGG AGTGGATTGG ATGGATTGAT

TATAACATCA GACACATCCT CCAACACAGC CTACCTGCAG CTCAGCAGCC

TGACATCTGA GGACACTGCC GTCTATTACT GTAGTAGGAG CGGTCCCGCC

TGGTTTGCTT ACTGGGGCCA AGGGACTCTG GTCACTGTCT CTGCAGCCAA

AACGACACCC CCATCTGTCT ATCCACTGGC CCCCCT
```

Amino Acid Sequence
```
SWWRSWADLV RPGALVKLSC KASGFNIKDF HMSWVKQRPE QGLEWIGWID

PENSNTIYDP KFQGKAIITS DTSSNTAYLQ LSSLTSEDTA VYYCSRSGPA

WFAYWGQGTL VTVS
```

Figure 33A

M 24 Light Chain Variable Region

Nucleotide Sequence

ATGACCCAGA CTCCACTCTC CCTGCCTGTC AGTCTTGGAG ATCAAGCCTC

CATCTCTTGC AGATCTAGTC AGACCATTGT ATATAGTAAT GGAAACACCT

ATTTAGAATG GTACCTGCAG AAACCAGGCC AGTCTCCAAA GCTCCTGATC

TACAAAGTTT CCAACCGATT TTCTGGGGTC CCAGACAGGT TCAGTGGCAG

TGGATCAGGG ACAGATTTCA CACTCAAGAT CAGCAGAGTG GAGTCTGAGG

ATCTGGGAAT TTATTACTGC TTTCAAGGTT CACATGTTCC TCGGACGTTC

GGTGGAGGCA CCAAGCTGGA AATCAAACGG

Amino Acid Sequence

MTQTPLSLPV SLGDQASISC RSSQTIVYSN GNTYLEWYLQ KPGQSPKLLI

YKVSNRFSGV PDRFSGSGSG TDFTLKISRV ESEDLGIYYC FQGSHVPRTF

GGGTKLEIKR

Figure 33B

M 24 Heavy Chain Variable Region

Nucleotide Sequence

```
GCTG GTGGAGATCA TGGGGCTGAA CTTGTGAGGC CAGGGGCCTT

AGTCAGGTTG TCCTGTAAAG CTTCTGGCTT CAACATTAAA GACTACCATA

TGTCCTGGCT GAAGCAGAGG CCTGAACAGG GCCTGGAGTG GATTGGATGG

ATTGATCCTG AGAATGGTAA TGCTATACAT GACCCGAAGT TCCAGGACAA

GGCCAATATA ACAGCAGACA CATCCTCCAA CACAGCCTAC CTGCAGCTCA

GCAGCCTGAC ATCTGAGGAC ACTGCCGTCT ATTTCTGTGC TAGATCGGGG

CCTGCCTGGT TTGCTTACTG GGGCCAAGGG ACTCTGGTCA CTGTCTCTGC

AGCCAAAACG ACACCCCCAT CTGTCTATCC ACTGGCCCC
```

Amino Acid Sequence

```
AGGDHGAE LVRPGALVRL SCKASGFNIK DYHMSWLKQR PEQGLEWIGW

IDPENGNAIH DPKFQDKANI TADTSSNTAY LQLSSLTSED TAVYFCARSG

PAWFAYWGQG TLVTVSAAKT TPPSVYPLAP
```

Figure 34

Amino Acid Sequence Comparisons and CDR Assignments of IgG Heavy Chain Variable Regions for Adiponectin Hybridoma Cell Lines M1 and M24

Framework 1:   1-24
CDR-1:         25-33
Framework 2    34-47
CDR-2:         48-64
Framework 3:   65-96
CDR-3:         97-104

Framework 1 / CDR-1

| | | | | | | | | | | | | | | | | | | | | | | | | |
|---|---|---|---|---|---|---|---|---|---|---|---|---|---|---|---|---|---|---|---|---|---|---|---|---|
| M1 | S | W | W | R | S | W | A | D | L | V | R | P | G | A | L | V | K | L | S | C | K | A | S | G | F | N | I | K | D |
| M24 | A | G | G | D | H | G |   | E |   |   |   |   |   |   |   |   | R |   |   |   |   |   |   |   |   |   |   |   |   |

CDR-1 / Framework 2 / CDR-2

| | | | | | | | | | | | | | | | | | | | | | | | |
|---|---|---|---|---|---|---|---|---|---|---|---|---|---|---|---|---|---|---|---|---|---|---|---|
| M1 | F | H | M | S | W | V | K | Q | R | P | E | Q | G | L | E | W | I | G | W | I | D | P | E | N | S | N | T | I | Y |
| M24 | Y |   |   |   |   | L |   |   |   |   |   |   |   |   |   |   |   |   |   |   |   |   |   |   |   | G |   | A |   | H |

CDR-2 / Framework 3

| | | | | | | | | | | | | | | | | | | | | | | | |
|---|---|---|---|---|---|---|---|---|---|---|---|---|---|---|---|---|---|---|---|---|---|---|---|
| M1 | D | P | K | F | Q | G | K | A | I | I | T | S | D | T | S | S | N | T | A | Y | L | Q | L | S | S | L | T | S | E |
| M24 |   |   |   |   |   | D |   | N |   |   | A |   |   |   |   |   |   |   |   |   |   |   |   |   |   |   |   |   |   |

Framework 3 / CDR-3

| | | | | | | | | | | | | | | | | | | | | |
|---|---|---|---|---|---|---|---|---|---|---|---|---|---|---|---|---|---|---|---|---|
| M1 | D | T | A | V | Y | Y | C | S | R | G | P | A | W | F | A | Y | W | G | Q | G | T | L | V | T | V | S |
| M24 |   |   |   |   |   | F | A |   |   |   |   |   |   |   |   |   |   |   |   |   |   |   |   |   |   |   |

Figure 35

Amino Acid Sequence Comparisons and CDR assignments of IgG Kappa Light Chain Variable Regions for Adiponectin Hybridoma Cell Lines M1 and M24

Framework 1     amino acids 1-20
CDR-1     amino acids 21-36
Framework 2     amino acids 37-51
CDR-2     amino acids 52-58
Framework 3     amino acids 59-90
CDR-3     amino acids 91-99

Framework 1 / CDR-1:

| | | | | | | | | | | | | | | | | | | | | | | |
|---|---|---|---|---|---|---|---|---|---|---|---|---|---|---|---|---|---|---|---|---|---|---|
| M1 | M | T | Q | T | P | L | S | L | P | V | S | L | G | D | Q | A | S | I | S | C | R | S | S | Q | S | I | V | Y | S | N |
| M24 | | | | | | | | | | | | | | | | | | | | | | | | | | | | | T | | |

CDR-1 / Framework 2 / CDR-2:

| | | | | | | | | | | | | | | | | | | | | | | |
|---|---|---|---|---|---|---|---|---|---|---|---|---|---|---|---|---|---|---|---|---|---|---|
| M1 | G | N | T | Y | L | E | W | Y | L | Q | K | P | G | Q | S | P | K | L | L | I | Y | K | V | S | N | R | F | S | G |
| M24 | | | | | | | | | | | | | | | | | | | | | | | | | | | | | | |

Framework 3:

| | | | | | | | | | | | | | | | | | | | | | | |
|---|---|---|---|---|---|---|---|---|---|---|---|---|---|---|---|---|---|---|---|---|---|---|
| M1 | V | P | D | R | F | S | G | S | G | S | G | T | D | F | T | L | K | I | S | R | V | E | A | E | D | L | G | V | Y |
| M24 | | | | | | | | | | | | | | | | | | | S | | | | | | I | | | | |

CDR-3:

| | | | | | | | | | | | | | | | | |
|---|---|---|---|---|---|---|---|---|---|---|---|---|---|---|---|---|
| M1 | Y | C | F | Q | G | S | H | V | R | R | T | F | G | G | G | T | K | L | E | I | R | R |
| M24 | | | | | | | | P | | | | | | | | | | K | | | | | |

Differences between the M1 and M24 hybridomas are indicated.

CHARACTERIZATION AND IDENTIFICATION OF UNIQUE HUMAN ADIPONECTIN ISOFORMS AND ANTIBODIES

PRIORITY TO RELATED APPLICATION(S)

This application claims the benefit of U.S. Provisional Application No. 60/879,179, filed Jan. 8, 2007, which is hereby incorporated by reference in its entirety.

FIELD OF THE INVENTION

The invention pertains to methods for measuring different forms of human adiponectin that are present in human plasma/serum, and more specifically methods are based on an ELISA assay that utilizes different monoclonal antibodies directed against adiponectin, in combination with different polyclonal antibodies directed against different domains of human adiponectin. The invention also provides unique isoforms of adiponectin and antibodies thereto, including polyclonal and monoclonal antibodies.

BACKGROUND OF THE INVENTION

Adiponectin is an adipocyte specific protein, that has recently been shown to possess a variety of activities including anti-inflammatory, antiatherogenic, preventive for metabolic syndrome, and insulin sensitizing activities. Adiponectin is encoded by a single gene, giving rise to a polypeptide chain of about 30 kilodaltons. In plasma/serum, adiponectin exists in various molecular forms that include monomers, trimer, hexamers, and various combinations thereof. No information is currently known in the art about which specific molecular forms of adiponectin possess which types of activities. While current ELISA methods exist to measure adiponectin levels in human plasma/serum, it is still not possible to accurately and rapidly measure the different adiponectin forms, nor are there useful adiponectin measures that predict the relationship of the levels of specific adiponectin forms to a specific physiologic state or disease. For example, current adiponectin measures include ELISA methods which measure total adiponectin, and do not provide a means of readily predicting the physiologic state based on the levels of adiponectin. Other measures such as velocity sedimentation or gel filtration, which can discriminate between high and low molecular weight adiponectin forms include complicated methods of fractionation on the basis of size, and are not readily amenable to high throughput screening procedures.

SUMMARY OF THE INVENTION

The present invention relates to the measurement of different adiponectin forms, specifically the ability to measure these forms in human plasma/serum. Additionally, the invention also provides the ability to correlate the levels of these different forms to a specific physiologic state, and preferably using the correlating levels of said different forms to diagnose individuals at risk of developing disease, including but not limited to diabetes, specifically Type II diabetes. Other potential disease indications where adiponectin isoforms may provide significant value include, but are not limited to metabolic syndrome, cardiovascular disease, inflammatory diseases, NASH (Nonalcoholic steatohepatitis), dyslipidemia, and other diseases.

The invention also provides unique isoforms of adiponectin and antibodies thereto, including polyclonal and monoclonal antibodies.

The invention also demonstrates that different adiponectin isoforms do exist, and that they can be readily measured using ELISA methods of the present invention.

As such, the utility of these assays, and the identified novel adiponectin antibodies and isoforms utilized therein, can be used to monitor disease progression, response to treatment, prediction of treatment responses, as well as the diagnosis of early forms of disease, more particularly diabetes and cardiovascular disease.

DESCRIPTION OF THE DRAWINGS

FIG. 1: Amino Acid Sequence of Human Adiponectin (SEQ ID NO: 16). The amino acid sequence of human adiponectin is shown, indicating the signal peptide cleavage site, and the start of the mature protein. The site of the potential N-linked N-glycosylation is shown in the figure.

FIG. 2: Schematic representation of different adiponectin molecular forms. Adiponectin has been shown to exist in multiple forms, ranging from a monomer, trimer, hexamer, as well as higher ordered aggregates. Any of the aggregate forms can have different conformations The functional role of these different molecular forms of adiponectin remains to be elucidated. It is not known whether there are additional post-translational modifications on adiponectin that modify either the molecular state or biological role of adiponectin.

FIG. 12: Standard curve for the ELISA assays using the adiponectin kit from R & D Systems. An example is provided of an ELISA standard curve using the commercially available adiponectin ELISA kit from R&D Systems.

FIG. 13: Fractionation of normal human plasma sample by velocity sedimentation, and measurement of adiponectin isoforms using the ELISA with MAB 3604. Human plasma was fractionated by velocity sedimentation, and fractions were collected. Fraction 1 is the top of the gradient, and fraction 20 is the bottom of the gradient. The adiponectin levels were measured using the MAB3604 in combination with the globular domain and the N-terminal domain polyclonal antibodies. The monoclonal antibody MAB3604 was used at a 1:5000 dilution as the capture antibody. 5 ul of each fraction was assayed to determine the levels of adiponectin.

FIG. 14: Fractionation of normal human plasma sample by velocity sedimentation, and measurement of adiponectin isoforms using the ELISA with mAb A12820. Human plasma was fractionated by velocity sedimentation, and fractions were collected. Fraction 1 is the top of the gradient, and fraction 20 is the bottom of the gradient. The adiponectin levels were measured using the mAb A12820 in combination with the globular domain, the N-terminal domain and C-terminal domain polyclonal antibodies. The monoclonal antibody mAb A12820 was used at 0.5 ug/ml as the capture antibody. 5 ul of each fraction was assayed to determine the levels of adiponectin.

FIG. 15: Fractionation of normal human plasma sample by velocity sedimentation, and measurement of adiponectin isoforms using the ELISA with MAB 10651. Human plasma was fractionated by velocity sedimentation, and fractions were collected. Fraction 1 is the top of the gradient, and fraction 20 is the bottom of the gradient. The adiponectin levels were measured using the MAB 10651 in combination with the globular domain, the N-terminal domain and C-terminal domain polyclonal antibodies. The monoclonal antibody MAB 10651 was used at 0.25 ug/ml as the capture antibody. 5 ul of each fraction was assayed to determine the levels of adiponectin.

FIG. 16: Fractionation of normal human plasma sample by velocity sedimentation, and measurement of adiponectin isoforms using the ELISA with mAb adiponectin M1. Human plasma was fractionated by velocity sedimentation, and fractions were collected. Fraction 1 is the top of the gradient, and fraction 20 is the bottom of the gradient. The adiponectin levels were measured using the mAb adiponectin M1 in combination with the globular domain, the N-terminal domain and C-terminal domain polyclonal antibodies. The mAb adiponectin M1 was used at 1.0 ug/ml as the capture antibody. 5 ul of each fraction was assayed to determine the levels of adiponectin.

FIG. 17: Fractionation of normal human plasma sample by velocity sedimentation, and measurement of adiponectin isoforms using the ELISA with mAb adiponectin M24. Human plasma was fractionated by velocity sedimentation, and fractions were collected. Fraction 1 is the top of the gradient, and fraction 20 is the bottom of the gradient. The adiponectin levels were measured using the mAb adiponectin M24 in combination with the globular domain, the N-terminal domain and C-terminal domain polyclonal antibodies. The monoclonal antibody mAb adiponectin M24 was used at 1.0 ug/ml as the capture antibody. 5 ul of each fraction was assayed to determine the levels of adiponectin.

FIG. 18: Fractionation of normal human plasma sample by velocity sedimentation, and measurement of adiponectin isoforms using the R & D adiponectin ELISA. Human plasma was fractionated by velocity sedimentation, and fractions were collected. Fraction 1 is the top of the gradient, and fraction 20 is the bottom of the gradient. The adiponectin levels were measured using the R & D adiponectin ELISA. The assay was used as described by the manufacturer. 5 ul of each fraction was assayed to determine the levels of adiponectin.

FIG. 32: Nucleic acid sequence (SEQ ID NO 4) and amino acid sequence (SEQ ID NO 19) of the M1 heavy chain variable region (FIG. 32b) and nucleic acid sequence (SEQ ID NO 5) and amino acid sequence (SEQ ID NO 18) of the M1 light chain variable region (FIG. 32a). The corresponding regions of the Adiponectin M1 hybridoma cDNA were cloned and sequenced. The amino acid sequence was deduced from the cDNA sequence. The variable region amino acids encode the specific binding region of the antibody, and confer the high degree of specificity of IgG binding to the adiponectin N-terminus amino acids.

FIG. 33: Nucleic acid sequence (SEQ ID NO 6) and amino acid sequence (SEQ ID NO 21) of the M24 heavy chain variable region (FIG. 33b) and nucleic acid sequence (SEQ ID NO 7) and amino acid sequence (SEQ ID NO 20) of the M24 light chain variable regions (FIG. 33a). The corresponding regions of the Adiponectin M1 hybridoma cDNA were cloned and sequenced. The amino acid sequence was deduced from the cDNA sequence. The variable region amino acids encode the specific binding region of the antibody, and confer the high degree of specificity of IgG binding to the adiponectin N-terminus amino acids.

FIG. 34: Amino Acid Sequence Comparisons and CDR Assignments of IgG Heavy Chain Variable Regions for Adiponectin Hybridoma Cell Lines M1 (SEQ ID NO: 19) and M24 (SEQ ID NO: 21), the comparison based on residues 1-114 of each said sequence.

FIG. 35: Amino Acid Sequence Comparisons and CDR Assignments of IgG Light Chain Variable Regions for Adiponectin Hybridoma Cell Lines M1 (SEQ ID NO: 18) and M24 (SEQ ID NO: 20).

Figure 3:
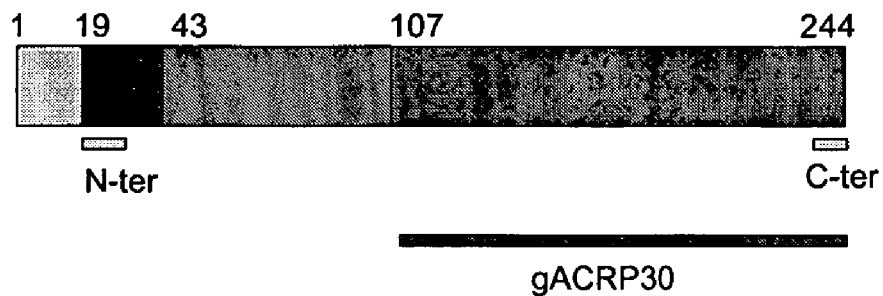
FIG. 3: Schematic representation of the various peptide sequences (SEQ ID NOS 1 (N-terminal) and 17 (C-terminal)) that were used (epitopes) to develop monoclonal and polyclonal antibodies. The specific sites that the commercial monoclonal antibodies are directed to are not known at present.

Table 1: Logistic regression and correlation results for the various adiponectin forms based on 126 Type II diabetics and 124 normal controls. Separate regression models were run for each form adjusting for age, body mass index (BMI) and insulin levels. Pearson correlation coefficients are presented for each form indicating the strength of it's relationship to fasting blood glucose.

DETAILED DESCRIPTION OF THE INVENTION

Definitions

All references cited herein are hereby incorporated by reference in their entirety.

The terms "protein" or "polypeptide" are intended to be used interchangeably. They refer to a chain of at least two (2) or more amino acids which are linked together via a peptide or amide bond, and is independent of post-translational modifications (e.g., glycosylation, acylation, phosphorylation, etc). Antibodies are specifically intended to be within the scope of this definition. The polypeptides of this invention may comprise more than one subunit, where each subunit is encoded by a separate DNA sequence. The protein may also encompass more than one polypeptide unit, comprising a dimer, trimer, tetramer, or various higher ordered structures. The different proteins may also be made up of additional proteins or components, for which we do not know the specific composition or identity.

"Isoform", refers to the different molecular forms proteins such as adiponectin, maybe found in human or animal, plasma, serum or other bodily fluids. The isoforms may also be produced by various recombinant methods, and be found secreted in the media from cells expressing adiponectin. For adiponectin, the isoform maybe comprised of multiple adiponectin subunits, and maybe modified by different post-translational modifications. The isoform may also consist of other proteins or components which together form a complex.

Adiponectin is an adipocyte specific protein that has recently been shown to possess a variety of activities including anti-inflammatory, antiatherogenic, preventive for metabolic syndrome, and insulin sensitizing activities. Adiponectin is encoded by a single gene, and consists of 244 amino acids, giving rise to a polypeptide chain of about 30 kilodaltons. The mature human adiponectin protein encompasses amino acids 19-244. A globular domain has been reported to encompass amino acids 107-244. In plasma/serum, adiponectin exists in various molecular forms that include monomers, trimers, hexamers, and various combinations thereof. No information is known in the art about which molecular forms of adiponectin possess which types of activities. While methods exist to measure adiponectin levels in human plasma/serum, it is still not possible to accurately measure the different adiponectin forms, nor to predict the relationship of the levels of specific adiponectin forms to a specific physiologic state or disease.

"Recombinant" adiponectin refers to proteins that are synthesized in cells that do not normally produce adiponectin. This technique is commonly used in the art for the preparation of large amounts of proteins for various types of studies. The "recombinant" adiponectin can be produced in E. coli, yeast, or various mammalian cell lines such as 293 or CHO cells. The recombinant adiponectin isoforms produced in these cell types can be similar to, or can differ significantly from the adiponectin isoforms present in human plasma samples.

"N-terminus" or "N-terminal" refers to the amino acid residues which are closest to the N-terminal of the protein. These residues will begin with amino acid residue 19 of the protein, and can contain as many as 40 additional amino acids. We utilized amino acid residues 19-39 of adiponectin as the N-terminal sequence, to which antibodies were developed.

"C-terminus" or "C-terminal" refers to the amino acid residues which are closest to the C-terminal of the protein. These residues will end with amino acid residue 244 of the protein, and can contain as many as 40 additional amino acids before the end of the protein. We utilized residues 223-244 of adiponectin as the C-terminal sequence, to which antibodies were developed.

The phrase "substantially identical" with respect to an antibody polypeptide sequence shall be construed as an antibody exhibiting at least 70%, preferably 80%, more preferably 90% and most preferably 95% sequence identity to the reference polypeptide sequence. The term with respect to a nucleic acid sequence shall be construed as a sequence of nucleotides exhibiting at least about 85%, preferably 90% more preferably 95% and most preferably 97% sequence identity to the reference nucleic acid sequence. For polypeptides, the length of the comparison sequences will generally be at least 25 amino acids. For nucleic acids, the length will generally be at least 75 nucleotides.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

The term "Insulin Sensitivity" as used herein refers to the measure of the body's ability to utilize glucose. This measure is dependent on the ability of insulin to stimulate glucose uptake. There are a variety of measures that can be used for this purpose, including fasting glucose, fasting insulin, oral glucose tolerance test, glucose clamp, or insulin clamp. All of these measures can be routinely used for this type of analysis.

The term "antigen" as used herein refers to the substance that stimulates an immune response, and that can be used to generate antibodies that specifically react with the antigen. The antibodies can be polyclonal or monoclonal in origin. Polyclonal antibodies are a group of antibody molecules that are produced from a large number of B cells, and are directed to a specific antigen. In polyclonal antibodies, there is a mixture of antibody molecules that recognize different epitopes or sequences of a protein or peptide. A monoclonal antibody is a single unique antibody molecule which is produced from a single B cell, and is directed specifically to an antigen, such as a protein or peptide.

The term "ELISA Assay" as used herein refers to enzyme linked immunosorbent assay. This assay is routinely used to measure levels of various entities, including proteins, peptides, and small molecules. It is not common to be able to identify different molecular forms of proteins, via traditional ELISA assays, other than post-translational modifications, such as phosphorylation, acylations, glcnacylation among others. Traditional ELISA methods do not have the ability to measure different molecular entities made up of the same subunit.

DETAILED DESCRIPTION OF THE INVENTION

The invention pertains to methods for measuring different forms of human adiponectin that are present in human plasma/serum, and more specifically methods are based on an ELISA assay that utilizes different monoclonal antibodies directed against adiponectin, in combination with different polyclonal antibodies directed against different domains of human adiponectin.

When different combinations of monoclonal and polyclonal antibodies are combined to configure an ELISA assay, the different ELISA formats can measure different molecular forms of adiponectin. Moreover, some of these different molecular forms of adiponectin correlate with different physiologic states. The levels of the different adiponectin molecular forms can be correlated with insulin sensitivity or fasting blood glucose, or with other physiologic states such as cardiovascular disease, steatosis, inflammation as well as other diseases.

The invention also provides unique isoforms of adiponectin and antibodies thereto, including polyclonal and monoclonal antibodies.

The methods of the invention are simple, reliable and reproducible, and are able to discriminate different adiponectin isoforms, including some forms (M1 globular, M1 N-terminus, M24 globular, M24 C-terminus, A12820 globular, A12820 N-terminus, A12820 C-terminus) which show a significant degree of correlation to the diabetic phenotype. Moreover, the invention demonstrates that prior methods which simply measure low or high molecular weight adiponectin isoforms is not sufficient to provide discriminatory power to identify individuals who have a form of type 11 diabetes. The assays of the invention can also be used to further define the association of adiponectin isoforms to other diseases such as cardiovascular disease, metabolic syndrome, inflammation, dyslipidemia, NASH, and others. The methods of the invention can also be used to monitor disease progression, response to treatment, prediction of treatment responses, as well as the diagnosis of early forms of disease.

As such, the utility of these assays, and the identified novel adiponectin antibodies and isoforms, can be used to monitor disease progression, response to treatment, prediction of treatment responses, as well as the diagnosis of early forms of disease.

Antibody Development & Characterization

Polyclonal antibodies were developed to the globular domain, N-terminal domain, and C-terminal domain of human adiponectin. These polyclonal antibodies can be used in Western blots and in the development of ELISAs for different forms of adiponectin that are found in body fluids, such as plasma, serum, etc. The polyclonal antibodies were raised in rabbits, and the procedure was performed by Pocono Rabbit Farm & Laboratory Inc, Canadensis, Pa., following standard protocols. The standard protocol was used for antigen injection, boosting, and bleeding. The antibodies were purified from serum by affinity chromatography with Protein G-Agarose. The antigen for the globular-domain was the recombinant adiponectin protein, encoding amino acid residues 107-244. The protein was produced in E. coli, and purified by standard purification techniques. The N-terminal peptide antigen has the N-terminal sequence ETTTQGPGVLLPLPKGASTGC. (SEQ ID NO: 1) The C-terminal peptide antigen has the sequence CYADNVNDSTFTGFLLYHDTN (SEQ ID NO: 2).

The novel monoclonal antibodies to human adiponectin N-terminus (N-ADIP M1 SEQ ID NOS 4 and 5, heavy and light chains respectively and M24 SEQ ID NOS 6 and 7, heavy and light chains respectively) were produced using the N-terminal sequence ETTQGPGVLLPLPKGAC (SEQ ID NO:3). These antibodies were produced in mice by Antibody Solutions, Mountain View, Calif. 94043. Antibody Solutions used their standard protocol (techniques which are well known in the art) for immunization (PolyExpress proprietary protocol for antibody response to antigen), production of hybridoma libraries (final boost of immune cells, fusion with myeloma cells, and cryopreservation), and monoclonal cultures (preparation of monoclonal cultures using flow cytometry cell sorting).

The protocols used are standard protocols for the generations, propagation, and characterization of hybridoma cells, according to the general procedural method below. (See also, Oi. V. T. and L. A. Herzenberg. 1979. In *Selected Methods in Cellular* Immunology. B. B. Mishell & S. M. Shiigi, eds. Freeman, San Francisco. p. 351, Reik, L. M., S. L. Maines. D. E. Ryan, W. Levin, S. Bandiera. and P. E. Thomas. 1987. A simple. non-chromatographic purification procedure for monoclonal antibodies. *J. Immunol. Methods* 100:123, said references hereby incorporated by reference). The primary screening of the hybridoma supernatants, was to detect reactivity of IgG in the hybridoma sups, with the N-terminal peptide coated onto 96 well plates. The secondary assay involved the capture of human adiponectin from plasma, followed by reactivity with polyclonal antibodies directed against human adiponectin, using an ELISA format. Monoclonal antibodies that were capable of capturing human adiponectin were deemed useful, and subsequently further characterized by ELISA analysis, and by western blot analysis.

ELISA Assay Development

The ELISA assays for measuring levels of human adiponectin rely on the ability to capture different adiponectin isoforms with specific monoclonal antibodies directed to adiponectin, and then to further identify the captured adiponectin isoforms with the use of different polyclonal antibodies that recognize different adiponectin epitopes. The configuration of these assays thus provides the ability to specifically recognize different adiponectin isoforms that are dependent on the ability of antibody pairs (a monoclonal antibody together with a polyclonal antibody) to specifically interact with unique adiponectin isoforms. We have used 5 different monoclonal antibodies (MAB3604 (Chemicon International), A12820(611645) (BD Biosciences), MAB10651 (R&D Systems, Inc), N-ADIP-M1 (Roche), and N-ADIP-M24 (Roche) in this analysis, coupled with three different polyclonal antibodies (N-terminal, C-terminal and globular). Thus we have the potential to develop 15 different assays, and to potentially identify 15 different adiponectin isoforms (M1 globular, M1 N-terminus, M1 C-terminus, M24 globular, M24 C-terminus, M24 N-terminus, A12820 globular, A12820 N-terminus, A12820 C-terminus, MAB10651 globular, MAB10651 N-terminus, MAB10651 C-terminus, MAB3604 globular, MAB 3604 N terminus). The combination of MAB 3604 C-terminus did not yield a signal. By using additional monoclonal and polyclonal antibodies, it is possible to identify even greater numbers of potential adiponectin isoforms.

Procedure for Generation of Rabbit Polyclonal Antibodies

Purified N-terminal or C-terminal adiponectin peptides were coupled to KLH, at a ratio of 1 mg of peptide to 1 mg of KLH via cysteine residues (conjugated peptide). 100-200 ug of conjugated peptide in complete freund's adjuvant (CFA) was injected intradermally into rabbits. 14 days later, 50-100 ug of conjugated peptide was injected intradermally in incomplete freund's adjuvant (IFA). 14 days later, 50-100 ug of conjugated peptide was injected intradermally in incomplete freund's adjuvant (IFA). The rabbits were bled 14 days later to obtain serum for analytical purposes. Thereafter, the rabbits were immunized subcutaneously every 30 days with 25-50 ug of conjugated peptide, then bled 14 days following immunization. The serum was collected, and then the IgG was purified as described below, and used in assay development. (reference for pAb production: Lui, F. T., Sinnecker, M., Hamaoka, J., and Katz, D. (1979) Biochemistry 18, 690-697. This is one of many protocols, which are standardly employed fro those skilled in the art). The antigens used were N-terminal adiponectin peptide, C-terminal adiponectin peptide, and recombinant globular adiponectin, spanning amino acids 107-244, produced in *E. coli.*

The above procedure resulted in the production of three different polyclonal antibodies, which we refer to as N-terminal, C-terminal, and globular antibodies, as discussed above in the "Antibody characterization and development" section. Each of these polyclonal antibodies was used together with different monoclonal antibodies, to generate a unique ELISA assay which recognized different adiponectin isoforms.

Procedure for Generation of Monoclonal Antibody

Immunization protocol and mAb production. Female BALB/c mice were immunized i.p. with 50 ug of conjugated N-terminal peptide in CFA and then boosted i.p. 5 wk later with 50 ug of conjugated N-terminal peptide in CFA. After 6 wk, 50 ug of conjugated N-terminal peptide in PBS was injected i.p. followed by an identical boost 48 h later. Two days after this last boost, the spleen was removed, teased into a cell suspension, and fused with the HAT-sensitive murine myeloma cell Sp2/0 as described previously (1 g). There are many similar procedures that are commonly used by those skilled in the art. Hybridomas were selected in HAT media, HB101 media (Irvine Scientific, Irvine, Calif.), 7% FBS, 2 mM glutamine, 1 mM sodium pyruvate, 1×HAT, and 10% Hybridoma Cloning Factor (HCF; IGEN, Rockville, Md.) (Kenney et al, Biotechnology, 13: 787, 1995). Aliquots of supernatant (50 ul) from wells exhibiting growth after 10 to 14 days were screened for anti-adiponectin N-terminal antibodies by ELISA. N-terminal peptide was coated on the bottoms of 96 well plates, and screened for reactivity with the hybridoma supernatants. Hybridomas which reacted with the N-terminal peptide were further screened by ELISA to determine whether they could interact with native adiponectin present in human plasma. Hybridomas of interest were cloned by limiting dilution in HAT media (Kenney et al, Biotechnology, 13: 787, 1995).

Ascitic fluid was produced by injecting cloned hybridomas into pristane-primed BALB/c mice (1-2×10E6 cells/mouse, i.p.). mAb were purified from heat-inactivated ascitic fluid by a combination of caprylic acid and ammonium sulfate precipitations as previously described (20). mAb were also produced by large scale culture, followed by protein-G chromatography to purify the IgG.

Optionally and preferably, a further enhancement to these protocols involves reversing the order of antibodies that are used in the assay. For example, the polyclonal antibodies can be used to capture different adiponectin isoforms, and then to further identify the captured adiponectin isoforms with the use of different monoclonal antibodies that recognize different adiponectin epitopes.

Quantification of the globular-, N-terminal-, and C-terminal domains of human adiponectin in plasma/serum and in fractions of plasma are measured in an ELISA format. Immunoplates are coated with one of the following monoclonal antibodies: MAB3604 (Chemicon International) at 1:5000 dilution, A12820(611645) (BD Biosciences) at 0.5 ug/ml, MAB10651 (R&D Systems, Inc) at 0.25 ug/ml, N-ADIP-M1 (Roche) at 1 ug/ml, and N-ADIP-M24 (Roche) at 1 ug/ml. The plates with 100 ul of the appropriate monoclonal antibody are covered with plate sealers and incubated at 4° C. for 16-20 hours. The plates are then washed 3 times with PBS—tween20 0.05% which is used for all subsequent washes. The plates were blocked with 300 ul of BSA 1%+Tween20 0.05% in PBS buffer for 1 hour and washed 3 times. The appropriate reference standards (0.0195 to 10 ng/well) are added to each plate in a final volume of 50 ul which is used for all subsequent incubations. For the globular and N-terminal domain of adiponectin detection, adiponectin (1-244) from R&D Systems (cat#1065, with his-tag on the C-terminus) is used. For the C-terminal adiponectin detection, adiponectin (16-247) from Alexis Biochemicals (cat#ALX-522-063, with an N-terminal FLAG tag) is used. Plasma/serum or plasma fraction is diluted in PBS with BSA 0.1%+Tween20 0.05% and added to each plate. The plates are incubated at 21-23° C. for 1 hour on an orbital shaker, and then washed 4 times. The appropriate detection antibody is added to each plate in PBS with BSA 0.1%+Tween20 0.05 and incubated at 21-23° C. for 1 hour on an orbital shaker followed by washing 4 times. The developing antibody, donkey anti-rabbit conjugated to horseradish-peroxidase, is added for 1 hour at 21-23° C. on an orbital shaker followed by 4 washes. The bound antibody conjugated to horseradish-peroxidase is quantified in the presence of 3,3',5,5'-tetramethylbenzidine (TMB). 50 ul of the TMB solution is added/well, the plates covered with plate sealers and incubated at 21-23° C. while shaking on a miniorbital plate shaker. The reaction is terminated at the appropriate time with the addition of 50 ul/well phosphoric acid 0.5M. The OD is read at 450 nm and the amount of adiponectin determined by interpolation from the appropriate standard curve. The reaction is terminated at a time which gives an OD reading of less than 2. This is between 2 and 10 minutes depending on the capture antibody and the detection antibody.

Screening Fractionated Plasma Samples

Plasma fractions from three normal donors were fractionated using a 5-20% sucrose gradients in 10 mM HEPES, pH 8, 125 mM NaCl were poured stepwise in 2-ml thin walled ultracentrifuge tubes (Becton Dickinson) and allowed to equilibrate overnight at 4° C. 600 ul of total plasma was diluted 1:10, applied and centrifuged on the gradient. Following layering of the sample on top (diluted 1:10 with 10 mM HEPES, pH 8, 125 mM NaCl), gradients were spun at 55,000 rpm for 4 h at 4° C. in a TLS55 rotor in a Beckman TL-100 tabletop ultracentrifuge (Pajvani et al 2004). 150-ul sample fractions were removed from the top of the tube, and labeled 1-20, with fraction 1 being the top of the gradient, while fraction 20 was on the bottom of the gradient. The gradient fractions were sequentially retrieved and analyzed by western or ELISA analysis as described below. Different antibodies were used for the western analysis, and were either monoclonal or polyclonal antibodies. For the ELISA analysis, each fraction was analyzed for the presence of adiponectin isoforms, by using an ELISA with different combinations of monoclonal antibody as a capture reagent, and different polyclonal antibodies as a developing reagent. The configuration can also be reversed, such that the polyclonal antibody is used as the capture antibody, and the monoclonal antibody is used as the developing antibody. A commercial human adiponectin ELISA (R&D Systems, Minneapolis, Minn.) was used for comparative purposes.

Screening Patient Plasma Collections

Collection of Human Plasma Samples

Both male and female diabetics and non-diabetics were recruited. Subjects were recruited following an overnight fast, and approximately 50 ml of blood was collected. The identity of the subjects was kept confidential (see informed consent form). The subjects include diabetics and age matched controls who are not diabetic.

Exclusion Criteria Both case and control subjects can not have type 1 diabetes or secondary forms of diabetes (e.g. Cushing's disease, acromegaly). Subjects undergoing steroid treatment or having inflammatory diseases (e.g. dermatomyositis) will be excluded. Subjects with a life expectancy less than one year (investigator judgment) will also be excluded. In addition to these criteria, control subjects can not have been previously diagnosed with type 2 diabetes or gestational diabetes, have a family history of type 2 diabetes, or have impaired fasting glucose or impaired glucose tolerance (as described above).

It is expected that the adiponectin isoforms and antibodies hereby divulged and utilized within the ELISA methods of the present invention will lead to a better understanding of the causes of certain diseases, including Type 2 Diabetes, and that this understanding should lead to better treatment and preventive measures.

Key Material and Parameters

For individuals who are known diabetics, a total of about 50 ml of blood was collected following an overnight fast.

If the individual has not previously been diagnosed with type 2 diabetes, or if they are a diet-treated diabetic, a total of about 50 ml of blood was collected following an overnight fast. Some individuals, were required to take a 75 gm oral glucose tolerance test. This test requires an overnight fast (at least 10 hours) and blood draws at 0, 30, and 120 minutes relative to administration of oral glucose. At most, a total of 60 mL of blood was drawn.

Procedure for Blood Collection and Plasma Preparation

Venous blood is withdrawn from the patients according to standard procedures. All steps were carried out consecutively as fast as possible to ensure maximum sample quality and to prevent proteolysis.

Per patient, ~50 ml of blood is collected (4×10 ml vacutainer). Every vacutainer is inverted twice to mix the blood with the anti-coagulant and immediately put on ice (not frozen).

After having finished the blood withdrawal, all vacutainers are immediately centrifuged for 15 min at 1500×g at 4° C.

The cooled (4° C. or on ice) vacutainers are opened and the supernatant is transferred to a 10 ml Falcon tube (on ice) using a 1 ml disposable tip pipette. Leave approx. 2 mm of supernatant to prevent carryover of the sediment.

Centrifuge the Falcon tubes for 30 min at 3000×g at 4° C. The centrifuge brake must be switched off.

The plasma supernatants in the Falcon Tubes were recovered with a pipette leaving all the sediment behind. All plasma samples were transferred to one 50 ml Falcon tube and gently mixed to ensure sample homogeneity.

The samples were shock-frozen in liquid nitrogen and stored in a −80° C. freezer. Shipment was on dry ice.

Screening

The human plasma samples were thawed and aliquoted into 96 wells in preparation for screening.

The assay procedure as described in the section Assay Development and as briefly outlined below was used in the in the standard curves for the assays FIGS. 7-12, and in the assays for the plasma fractions, FIGS. 13-18. The assay format was also used in determining the levels of adiponectin in the human plasma sample collections for correlation to disease state, FIG. 19-31.

1) Appropriate capture antibody added to an immunoplate in a volume of 100 ul PBS for 16-20 hours at 4° C.
2) Aspirate and wash the plate 3 times
3) Plate blocked with BSA 1%+Tween20 0.05%+PBS in a volume of 300 ul for 1 hour at 21-23° C. in a volume of 300 ul.
4) Aspirate and wash the plate 3 times
5) Appropriate reference standards added to each plate with dilutions in BSA 0.1%+Tween20 0.05%+PBS in a final volume of 50 ul.
6) Plasma/serum added to each plate with dilutions in BSA 0.1%+Tween20 0.05%+PBS in a final volume of 50 ul.
7) Plate placed on an orbital shaker and incubated at 21-23° C. for 1 hour.
8) Aspirate and wash the plate 4 times
9) Appropriate detection antibody added to each plate in BSA 0.1%+Tween20 0.05%+PBS in a final volume of 50 ul and placed on an orbital shaker and incubated at 21-23° C. for 1 hour
10) Aspirate and wash the plate 4 times
11) Developing antibody, donkey anti-rabbit-HRP, added to each plate in BSA 0.1%+Tween20 0.05%+PBS in a final volume of 50 ul and placed on an orbital shaker and incubated at 21-23° C. for 1 hour
12) Aspirate and wash the plate 4 times
13) TMB substrate solution added to the plate in a volume of 50 ul and placed on an orbital shaker and incubated at 21-23° C. until the appropriate development time
14) The reaction is terminated by adding phosphoric acid 0.5M in a volume of 50 ul
15) The OD is read at 450 nm and the amount of adiponectin determined by interpolation from the standard curve.

Quantification of the different human adiponectin isoforms in plasma/serum and in fractions of plasma are measured in an ELISA format. Immunoplates are coated with one of the following monoclonal antibodies: MAB3604 (Chemicon International) at 1:5000 dilution, A12820(611645) (BD Biosciences) at 0.5 ug/ml, MAB10651 (R&D Systems, Inc) at 0.25 ug/ml, N-ADIP-M1 (Roche) at 1 ug/ml, and N-ADIP-M24 (Roche) at 1 ug/ml. The plates with 100 ul of the appropriate monoclonal antibody are covered with plate sealers and incubated at 4° C. for 16-20 hours. The plates are then washed 3 times with PBS—tween20 0.05% which is used for all subsequent washes. The plates were blocked with 300 ul of BSA 1%+Tween20 0.05% in PBS buffer for 1 hour and washed 3 times. The appropriate reference standards (0.0195 to 10 ng/well) are added to each plate in a final volume of 50 ul which is used for all subsequent incubations. For the globular and N-terminal domain of adiponectin detection, adiponectin (1-244) from R&D Systems (cat#1065, with his-tag on the C-terminus) is used. For the C-terminal adiponectin detection, adiponectin (16-247) from Alexis Biochemicals (cat#ALX-522-063, with an N-terminal FLAG tag) is used. Plasma/serum or plasma fraction is diluted in PBS with BSA 0.1%+Tween20 0.05% and added to each plate. The plates are incubated at 21-23° C. for 1 hour on an orbital shaker, and then washed 4 times. The appropriate detection antibody is added to each plate in PBS with BSA 0.1%+Tween20 0.05 and incubated at 21-23° C. for 1 hour on an orbital shaker followed by washing 4 times. The developing antibody, donkey anti-rabbit conjugated to horseradish-peroxidase, is added for 1 hour at 21-23° C. on an orbital shaker followed by 4 washes. The bound antibody conjugated to horseradish-peroxidase is quantified in the presence of 3,3',5,5'-tetramethylbenzidine (TMB). 50 ul of the TMB solution is added/well, the plates covered with plate sealers and incubated at 21-23° C. while shaking on a miniorbital plate shaker. The reaction is terminated at the appropriate time with the addition of 50 ul/well phosphoric acid 0.5M. The OD is read at 450 nm and the amount of adiponectin determined by interpolation from the appropriate standard curve. The reaction is terminated at a time which gives an OD reading of less than 2. This is between 2 and 10 minutes depending on the capture antibody and the detection antibody, and their concentrations.

Sequencing of Variable Heavy and Light Chian cDNAs for Adiponectin Hybrodomas M1 and M24

Materials and Methods:

Hybridoma cells were grown and total RNA extracted by standard procedures. See, e.g., "Characterization of a murine monoclonal antibody that mimics heparin-induced thrombocytopenia antibodies".

G. M. Arepally, S. Kamei, K. S. Park, K. Kamei, Z. Q. Li, W. Liu, D. L. Siegel, W. Kisiel, D. B. Cines and M. Poncz BLOOD (Mar. 1, 2000) Volume 95 Number 5 pp. 1533-1540

"Efficient amplification and direct sequencing of mouse variable regions from any immunoglobulin family"

Thierry Chardes, Sylvie Villard, Gaelle Ferrieres, Marine Piechaczyk, Marine Cerutti, Gerard Devauchelle and Bernard Pau FEBS Letters 452 (1999) pp. 386-394

First strand cDNA was synthesized by standard procedures, using either oligo dT or the reverse PCR oligos as primers. Variable heavy and light chain region cDNAs were PCR amplified using the following conditions:

94C/5 minutes

94C/30 seconds

55C/30 seconds

72C/90 seconds 30 cycles

72C/10 minutes

The following PCR oligos were used:

From Ref 1:

```
                                          (SEQ ID NO: 8)
Heavy chain Framework 1 (forward primer)
GAG GTG AAG CTG GTG GAG (AT )C( AT) GG (SEQ ID NO: 9)
Heavy chain constant (reverse primer)
GGG GCC AGT GGA TAG AC (SEQ ID NO: 10)
Light chain Framework 1 (forward primer)
CCA GTT CCG AGC TCC AGA TGA CCC AGA CTC CA (SEQ ID NO: 11)
Light chain constant (reverse primer)
GTT GGT GCA GCA TCA GC
```

From Ref 2:

```
                                                         (SEQ ID NO: 12)
Heavy chain Framework 1 (forward primer)
CAG GT( GC) (AC )A( GA) CTG (GC )(A T)G (GC )AG (TA )C( AT)
 GG (SEQ ID NO: 13)
Heavy chain constant (reverse primer)
CGA CAA GTC GAC TAG CCC TTG ACC AGG CAT CC (SEQ ID NO: 14)
Light chain Framework 1 (forward primer)
GAG ATT (CG )AG CT( GC) ACC CAG TCT CCA (SEQ ID NO: 15)
Light chain constant (reverse primer)
CGA CTA GTC GAC TGG TGG GAA GAT GGA TAC AG
```

Products were analyzed by agarose gel electrophoresis. Light chain amplicons were gel isolated and sequenced uncloned. Heavy chain amplicons were subcloned, and the sequences determined from cloned plasmids.

Results

Assay Development and Standardization

Figure 4:
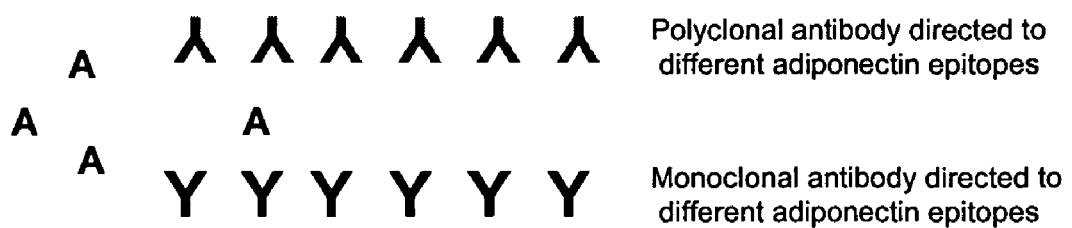
FIG. 4: Schematic representation of the adiponectin assay format. Briefly, monoclonal antibodies directed to adiponectin, are used to coat multiwell plates at a concentration of 0.1-10 ug/well. After a coating period of 2 hours-2 days, the wells are rinsed with buffer, and the biologic sample containing adiponectin is added to the plate, and incubated with antibody coated plate for several hours. The wells are washed with buffer, and a rabbit polyclonal antibody directed to different epitopes of adiponectin is added to the wells, and incubated for an hour. The wells are washed with buffer, and a developing antibody, donkey antirabbit IgG conjugated to HRP is added for an hour. The wells are washed several times, and a TMB substrate solution is added for a fixed time. The reaction is stopped with the addition of phosphoric acid, and the optical density at 450 nm is determined. The amount of adiponectin in the sample is determined by comparing the OD (optical density) of the sample, to the OD of a known amount of adiponectin which is used to generate a standard curve.
Figure 5:
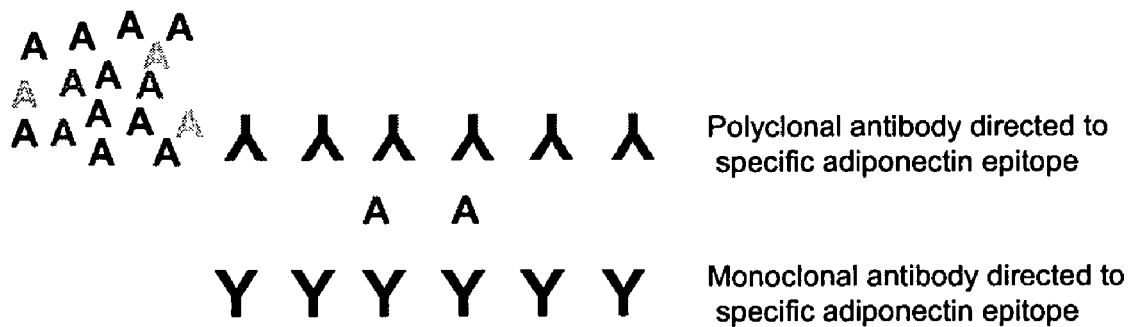
FIG. 5: Schematic representation of a selective adiponectin assay. Specific combinations of antibodies are used to detect specific adiponectin forms within the mixture of adiponectin, which is generally found in biologic samples such as plasma. Only adiponectin isoforms recognized by two antibodies, one of which is a monoclonal antibody, and a second which is a polyclonal antibody, will be recognized and quantitated in these assays. There may be examples where certain combinations of antibodies are able to recognize multiple forms of adiponectin. One example of such an assay could be the commercial adiponectin assay from R&D systems, or some of the assays which we have developed, which recognize multiple forms of adiponectin (based on levels of adiponectin measured, as well as the different isoforms that are recognized from gradient fractionated plasma).

Different assays for human adiponectin were developed. The assay format used was an ELISA assay, which utilizes a specific monoclonal antibody as a capture antibody, a solution containing the adiponectin, such as a suitable standard, or human plasma or serum, followed by the addition of a polyclonal antibody (FIGS. 4 & 5). Each combination of monoclonal and polyclonal antibody represents a different assay format. The specific combination of monoclonal antibody, coupled with a polyclonal antibody, provides for a specific adiponectin assay (FIG. 5). In some instances, the specific combination will not be able to measure adiponectin at all (such as the combination of MAB3604 C-terminus), while with others different levels of adiponectin are measured.

To facilitate development of the ELISAs, we developed novel monoclonal antibodies that are specific for the N-terminus of adiponectin. These mAbs reacted specifically with N-terminal adiponectin peptide, and also specifically reacted with adiponectin as determined by ELISA, western blot analysis, and immunofluorescence. These mAbs were further used in combination with polyclonal antibodies to measure levels of adiponectin in human plasma using ELISA assays.

Figure 6:
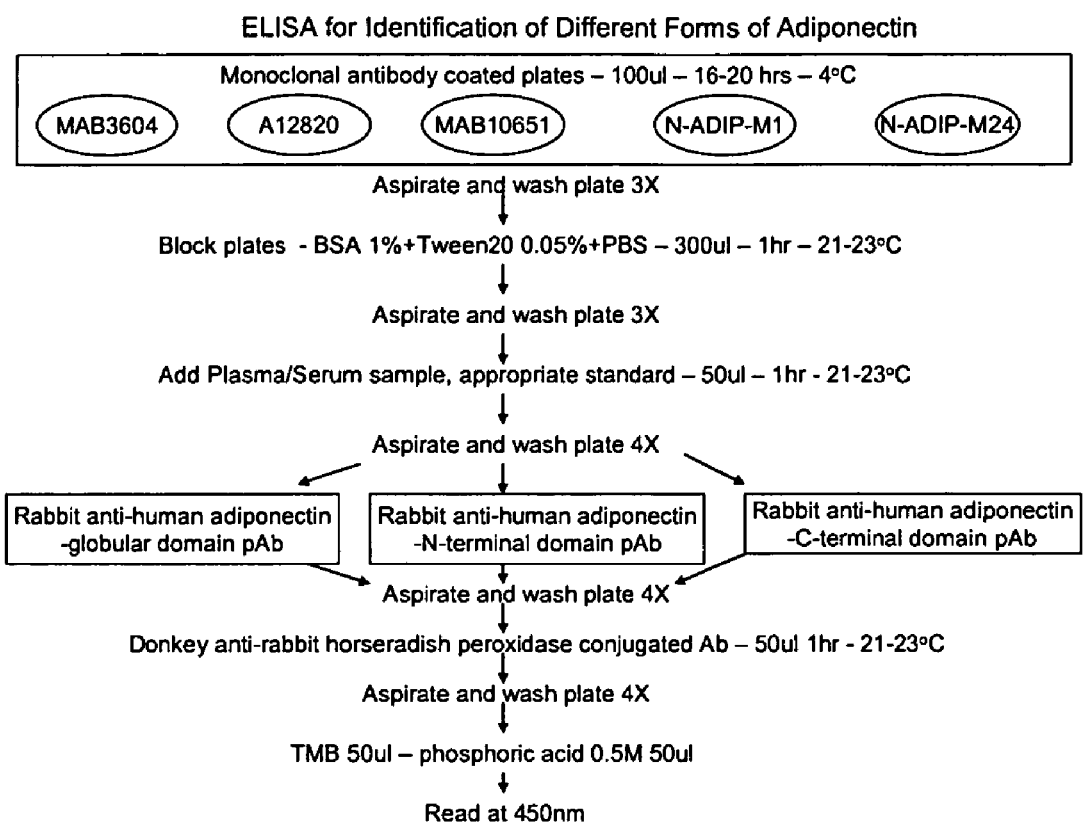
FIG. 6: Schematic representation of the work flow in measuring adiponectin levels in plasma samples.
Figure 7A:
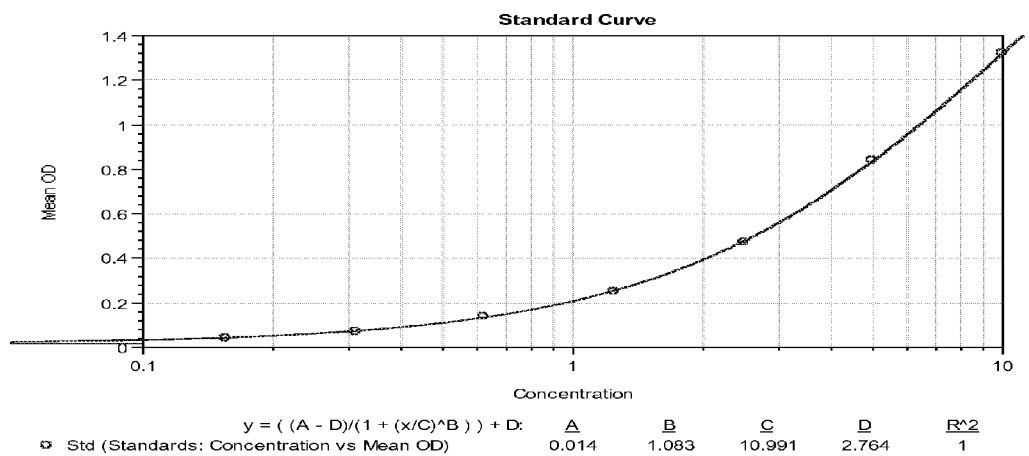
FIG. 7: Standard curve for ELISA assays using MAB3604 and globular and N-terminal polyclonal antibodies. Examples are provided of an ELISA standard curve using the reference adiponectin 1-244 standard (C-term His-tag) 0.0195 to 10 ng/well for the globular domain adiponectin pAb (FIG. 7*a*), and (FIG. 7*b*) for the N-terminal domain adiponectin pAb with the mAb MAB3604 at a 1:5000 dilution.
Figure 7B:
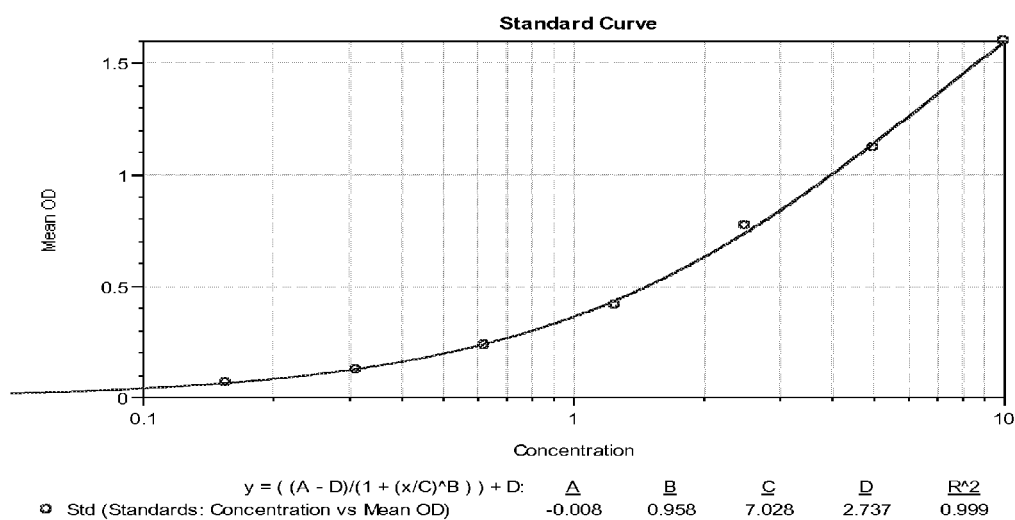
Figure 8A:
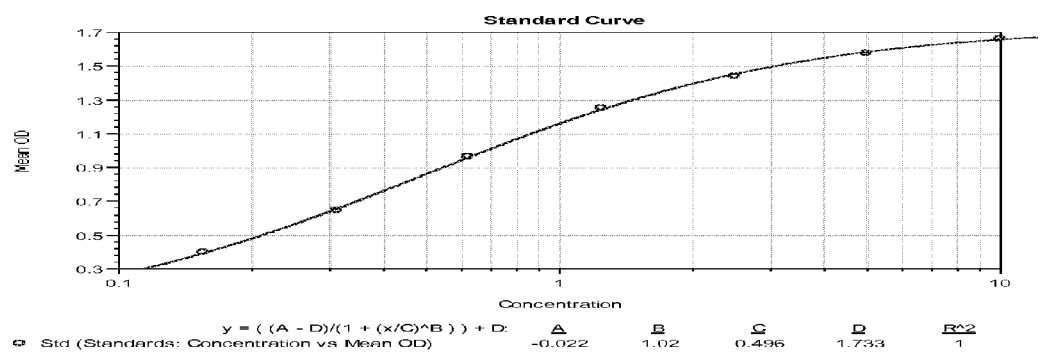
FIG. 8: Standard curve for ELISA assays using mAb A12820 and three anti-adiponectin polyclonal antibodies. Examples are provided of an ELISA standard curve using the reference standard adiponectin 1-244 (C-term His tag) 0.0195 to 10 ng/well for the adiponectin globular domain pAb (FIG. 8*a*), and (FIG. 8*b*) for the N-terminal domain adiponectin pAb.
FIG. 8*c* is an example of a standard curve using the reference standard adiponectin 16-247 (N-term FLAG tag) 0.0195 to 10 ng/well for the C-terminal domain adiponectin pAb. The mAb used in each example is A12820 at 0.5 ug/ml.
Figure 8B:
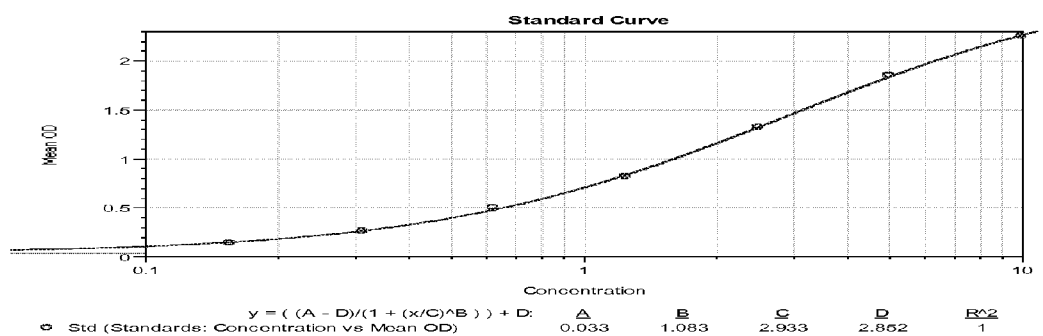
Figure 8C:
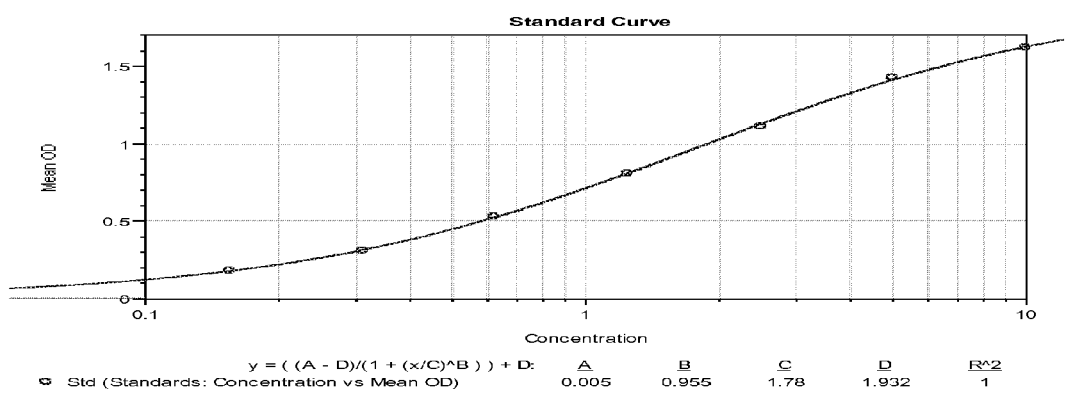
Figure 9A:
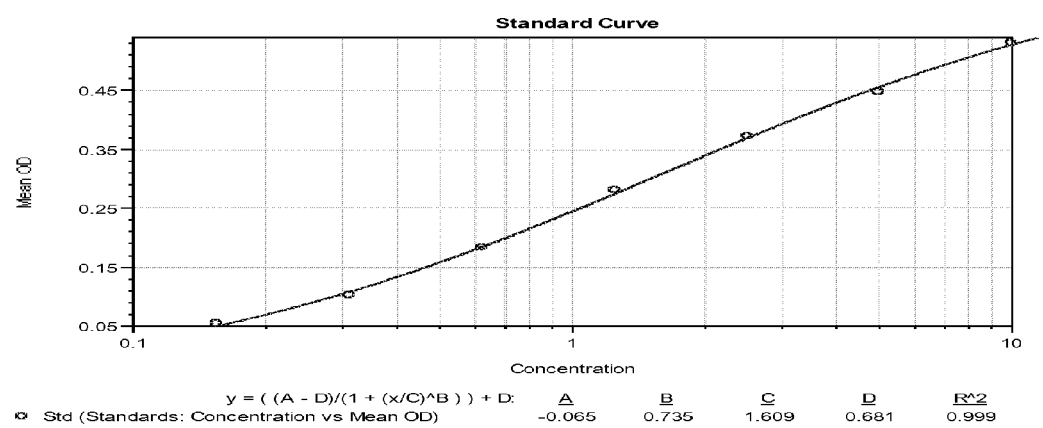
FIG. 9: Standard curve for ELISA assays using mAb MAB10651 and three anti-adiponectin polyclonal antibodies. Examples are provided of an ELISA standard curve using the reference standard adiponectin1-244 (C-term His tag) 0.0195 to 10 ng/well for the adiponectin globular domain pAb (FIG. 9*a*), and (FIG. 9*b*) for the N-terminal domain pAb.
FIG. 9*c* is an example of a standard curve using the reference standard adiponectin 16-247 (N-term FLAG tag) for the C-terminal domain adiponectin pAb. The mAb is MAB10651 at 0.25 ug/ml.
Figure 9B:
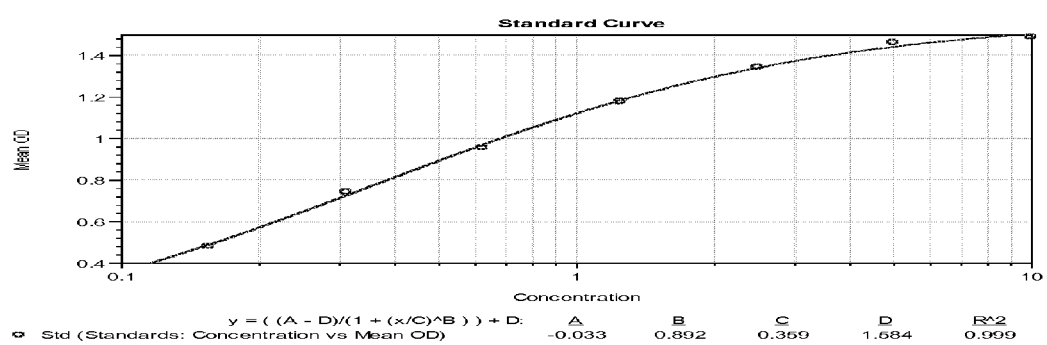
Figure 9C:
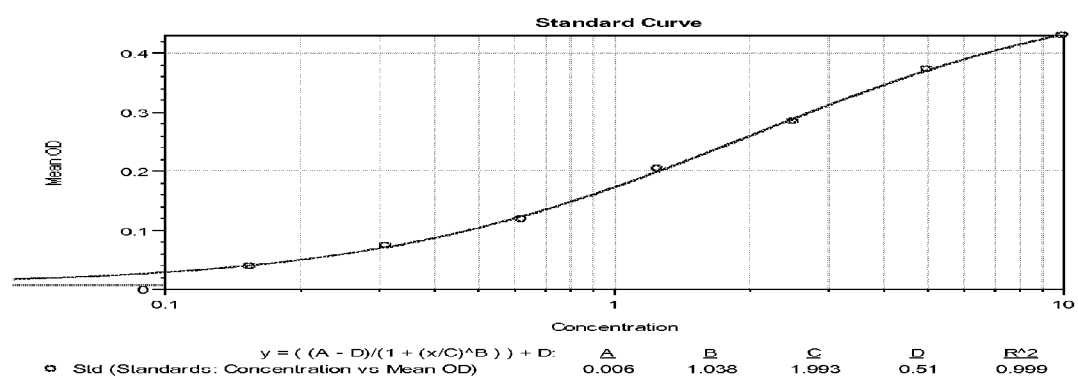
Figure 10A:
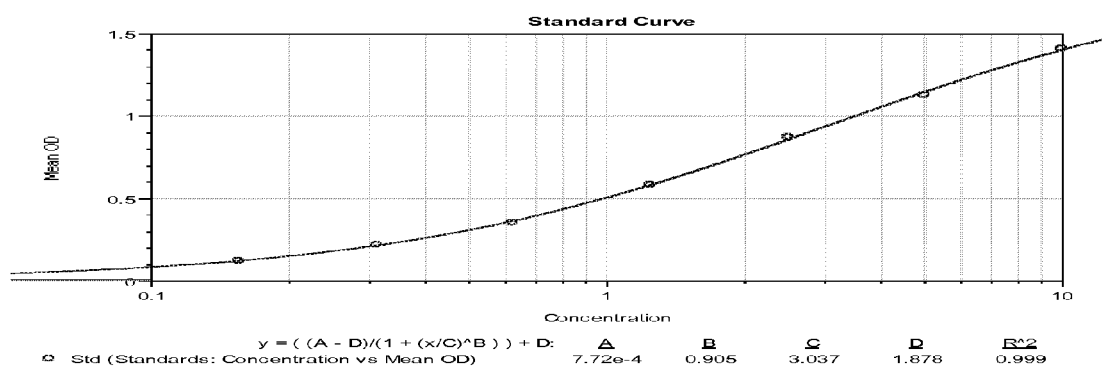
FIG. 10: Standard curve for ELISA assays using mAb Adiponectin M1 and three anti-adiponectin polyclonal antibodies. Examples are provided of an ELISA standard curve using the reference standard adiponectin1-244 (C-term His tag) 0.0195 to 10 ng/well for the adiponectin globular domain pAb, and (FIG. 10*a*), and (FIG. 10*b*) for the N-terminal domain pAb.
FIG. 10*c* is an example of a standard curve using the reference standard adiponectin 16-247 (N-term FLAG tag) for the C-terminal domain adiponectin pAb. The mAb is Adiponectin-M1 at 1 ug/ml.
Figure 10B:
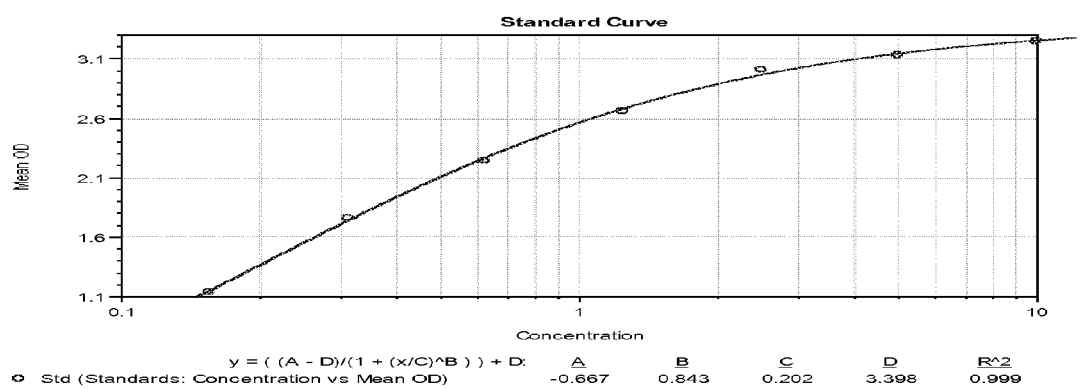
Figure 10C:
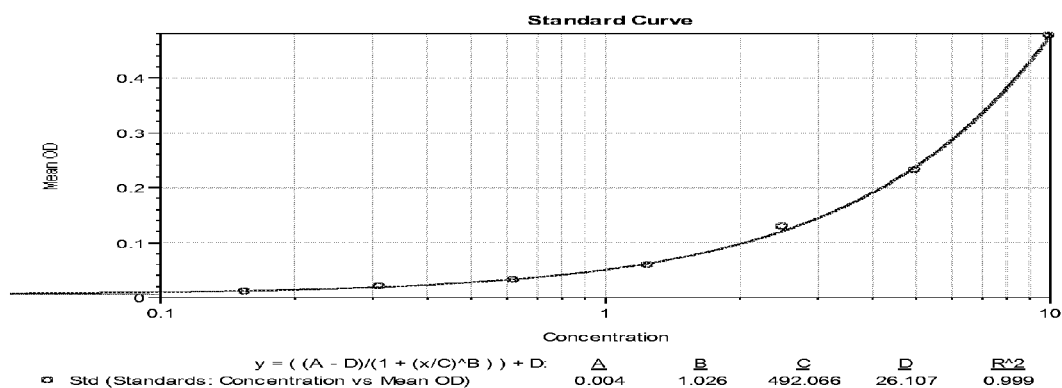
Figure 11A:
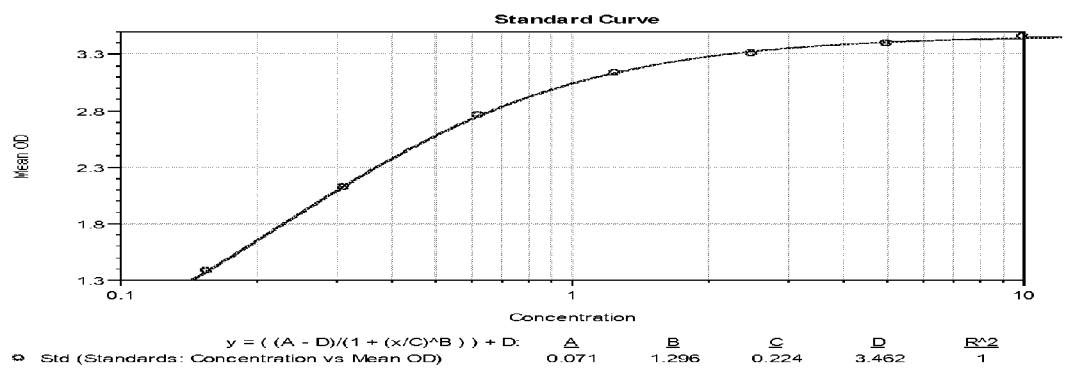
FIG. 11: Standard curve for ELISA assays using mAb Adiponectin M24 and three anti-adiponectin polyclonal antibodies. Examples are provided of an ELISA standard curve using the reference standard adiponectin1-244 (C-term His tag) 0.0195 to 10 ng/well for the adiponectin globular domain pAb (FIG. 11*a*), and (FIG. 11*b*) for the N-terminal domain pAb.
FIG. 11*c* is an example of a standard curve using the reference standard adiponectin 16-247 (N-term FLAG tag) for the C-terminal domain adiponectin pAb. The mAb is Adiponectin-M24 at 1 ug/ml.
Figure 11B:
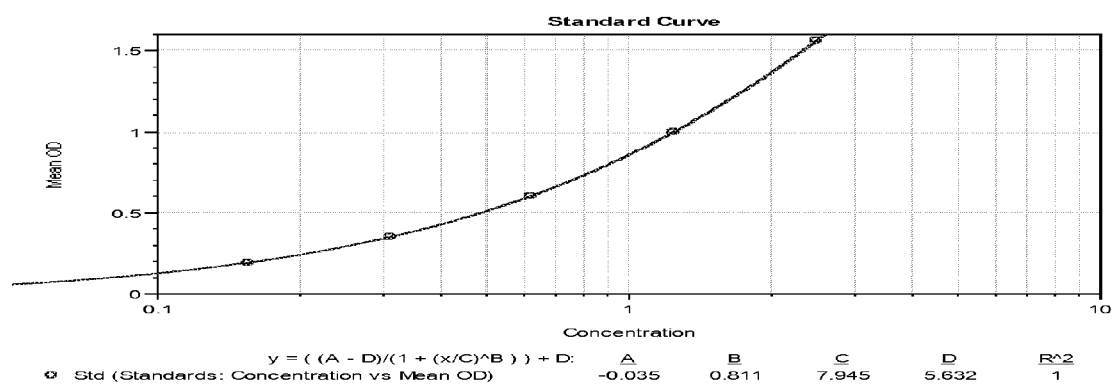
Figure 11C:
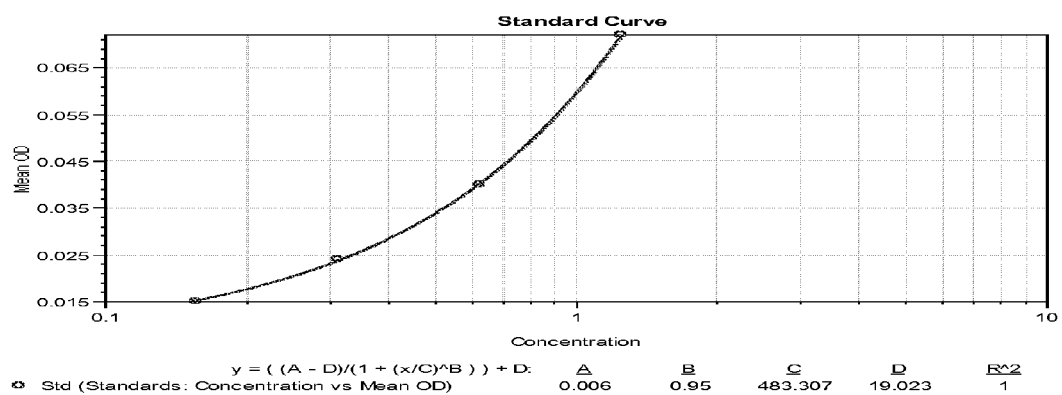
Figure 19A:
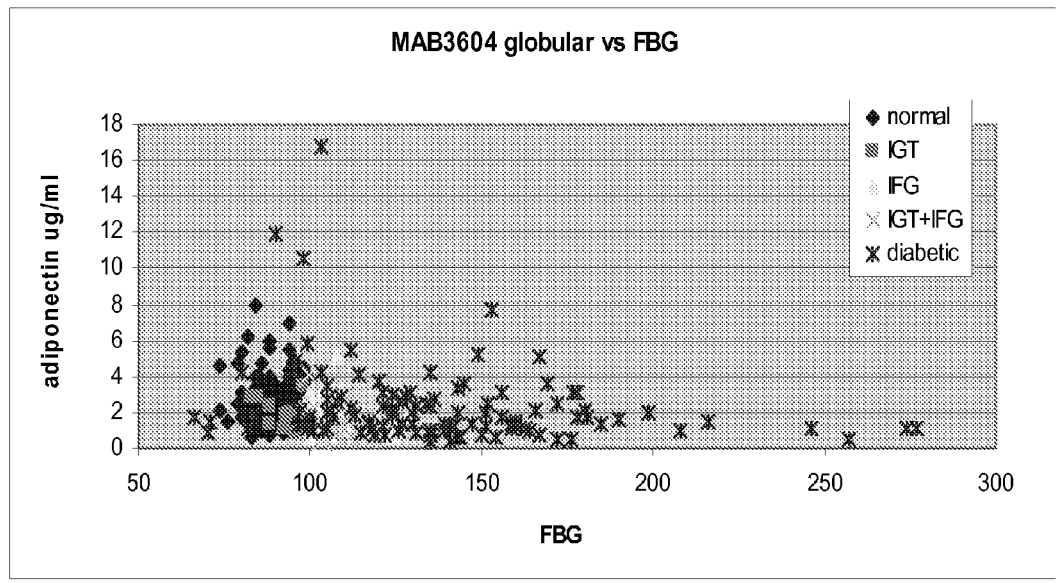
FIG. 19: Analysis of human plasma samples for adiponectin levels using MAB 3604 with globular and N-terminal adiponectin polyclonal antibodies. Human fasting plasma samples collected from normal, diabetic, impaired glucose tolerant (IGT), impaired fasting glucose (IFG) and both IGT & IFG individuals was assayed for levels of adiponectin. The antibody pairs for assaying were MAB 3604 in combination with globular adiponectin (FIG. 19*a*) or N-terminal adiponectin (FIG. 19*b*) polyclonal antibodies. The adiponectin levels (ug/ml) are plotted against the levels of fasting blood glucose (mg/dL). Individuals with normal fasting glucose levels—diamond, IGT—square, IFG—triangles, IGT+IFG—cross, and diabetic—asterisk. No significant correlation is apparent.
Figure 19B:
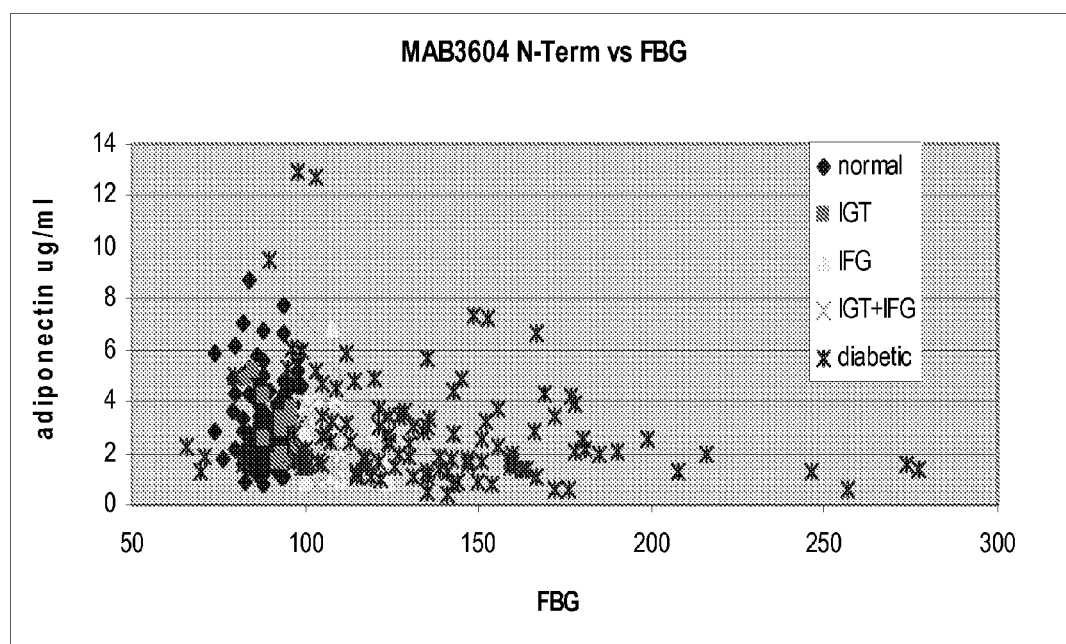
Figure 20A:
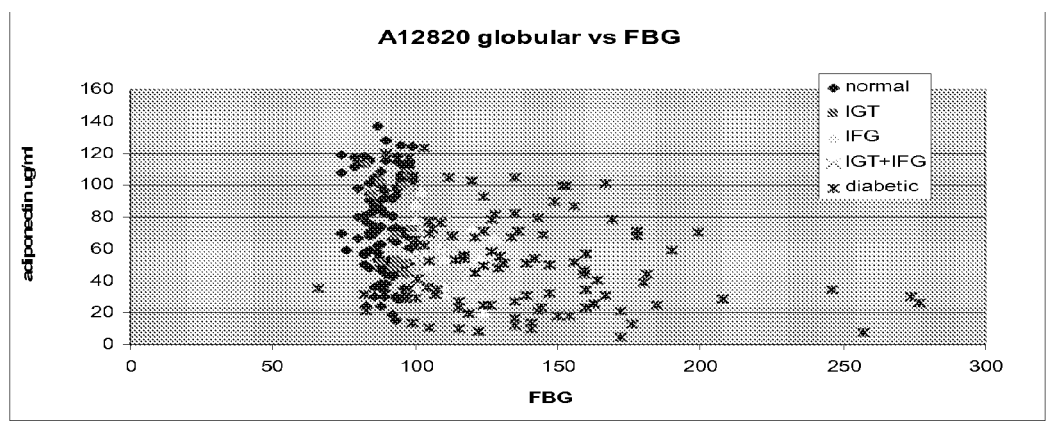
FIG. 20: Analysis of human plasma samples for adiponectin levels using mAb A12820 with globular, N-terminal and C-terminal adiponectin polyclonal antibodies. Human fasting plasma samples collected from normal, diabetic, impaired glucose tolerant (IGT), impaired fasting glucose (IFG) and both IGT & IFG individuals was assayed for levels of adiponectin. The antibody pairs for assaying were mAb A12820 in combination with globular adiponectin (FIG. 20a), N-terminal (FIG. 20b), or C-terminal (FIG. 20c), adiponectin polyclonal antibodies. The adiponectin levels (ug/ml) are plotted against the levels of fasting blood glucose (mg/dL). Individuals with normal fasting glucose levels—diamond, IGT—square, IFG—triangles, IGT+IFG—cross, and diabetic—asterisk. A significant correlation is apparent, especially with the N and C-terminal antibodies.
Figure 20B:
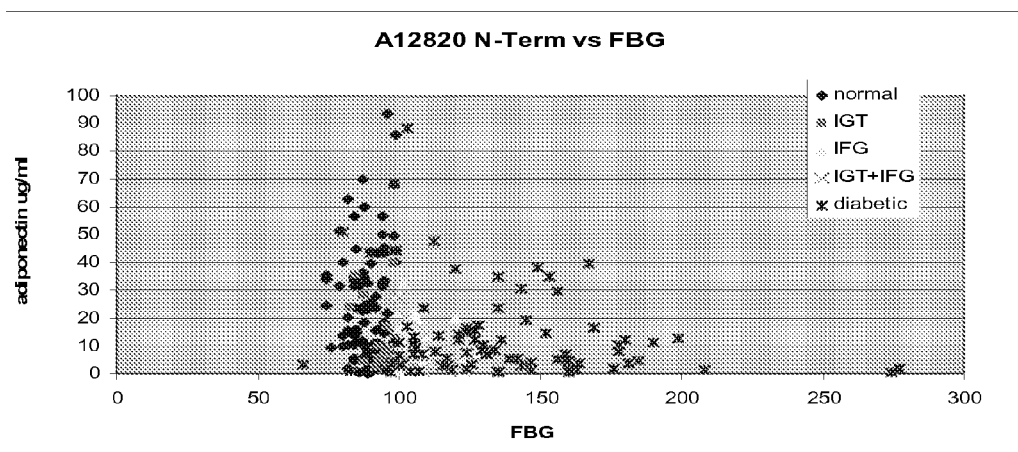
Figure 20C:
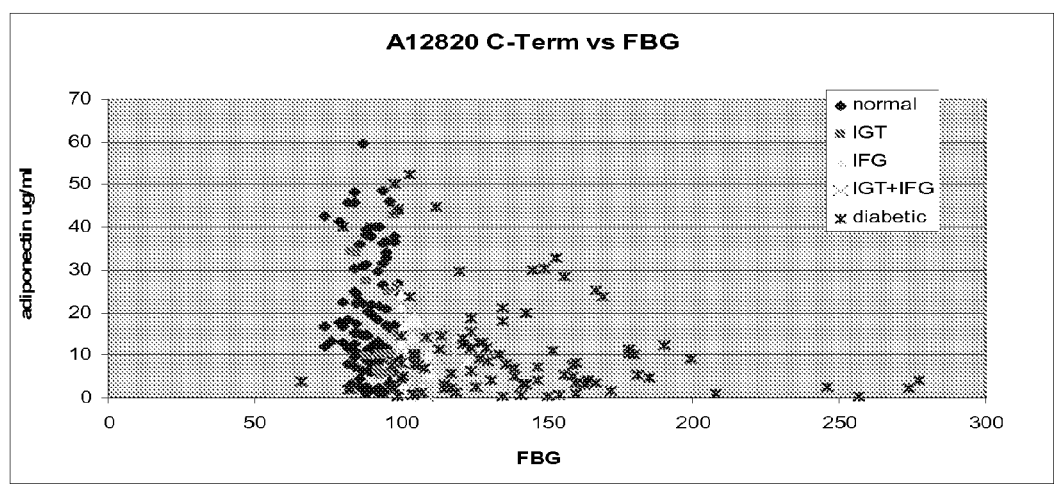
Figure 21A:
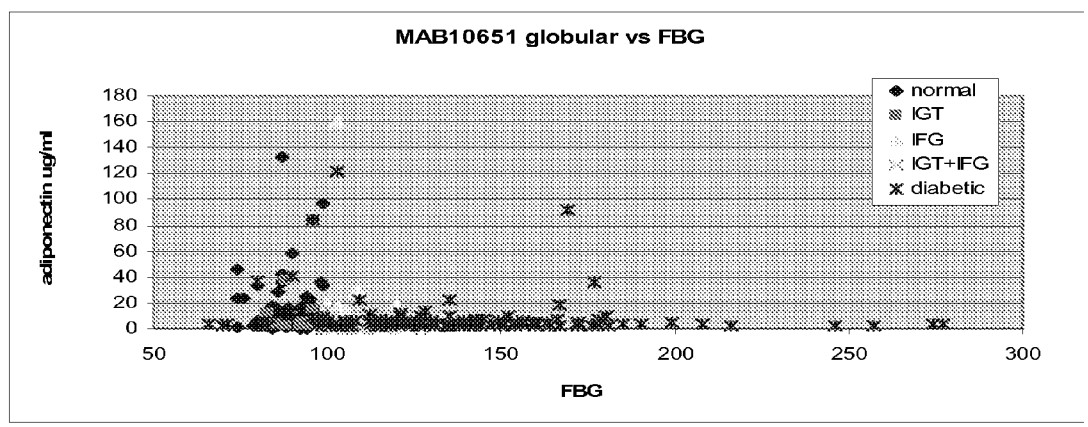
FIG. 21: Analysis of human plasma samples for adiponectin levels using MAB 10651 with globular, N-terminal and C-terminal adiponectin polyclonal antibodies. Human fasting plasma samples collected from normal, diabetic, impaired glucose tolerant (IGT), impaired fasting glucose (IFG) and both IGT & IFG individuals was assayed for levels of adiponectin. The antibody pairs for assaying were MAB 10651 in combination with globular adiponectin (FIG. 21a), N-terminal (FIG. 21b), or C-terminal (FIG. 21c), adiponectin polyclonal antibodies. The adiponectin levels (ug/ml) are plotted against the levels of fasting blood glucose (mg/dL). Individuals with normal fasting glucose levels—diamond, IGT—4 square, IFG—triangles, IGT+IFG—cross, and diabetic—asterisk. No significant correlation is apparent.
Figure 21B:
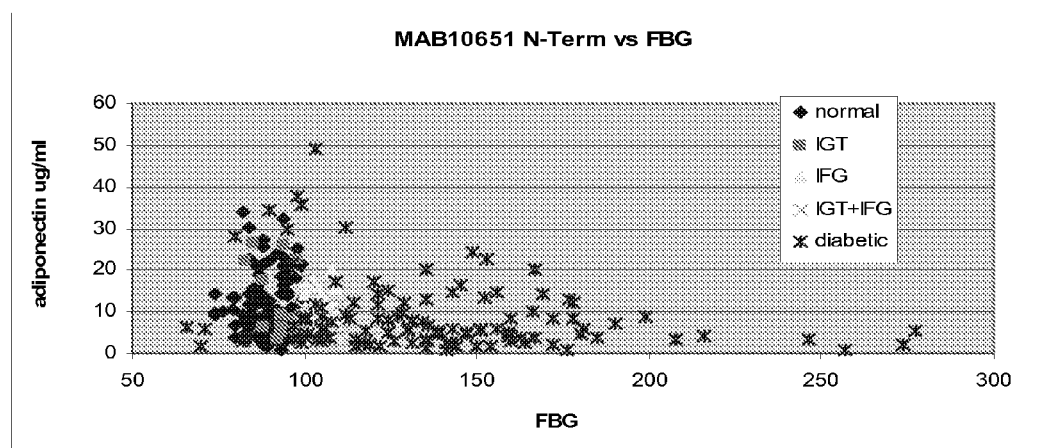
Figure 21C:
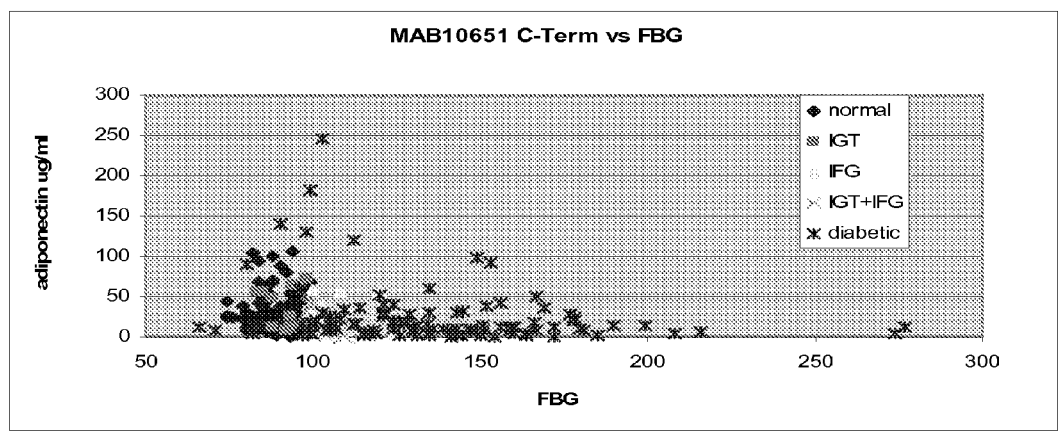
Figure 22A:
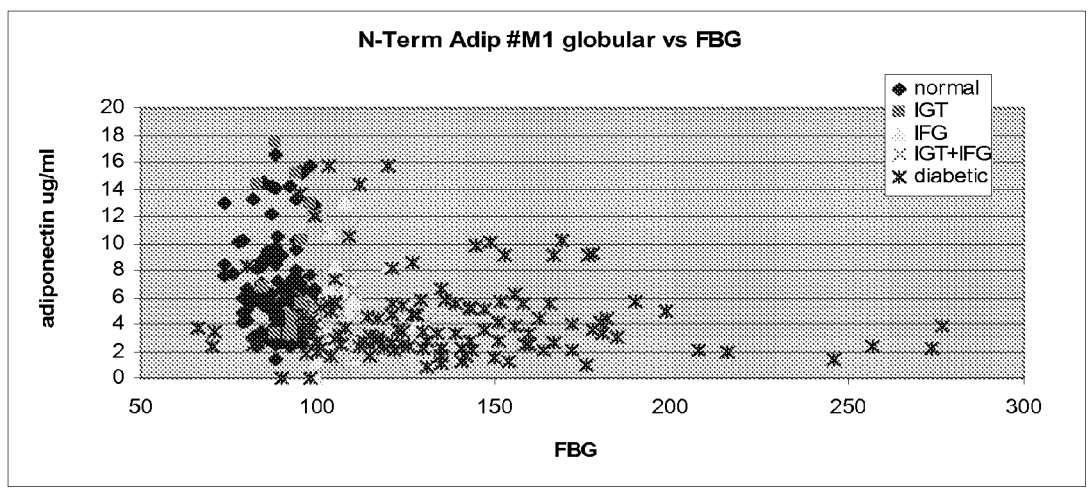
FIG. 22: Analysis of human plasma samples for adiponectin levels using mAb adiponectin M1 with globular, N-terminal and C-terminal adiponectin polyclonal antibodies. Human fasting plasma samples collected from normal, diabetic, impaired glucose tolerant (IGT), impaired fasting glucose (IFG) and both IGT & IFG individuals was assayed for levels of adiponectin. The antibody pairs for assaying were mAb adiponectin M1 in combination with globular adiponectin (FIG. 22a), N-terminal (FIG. 22b), or C-terminal (FIG. 22c) adiponectin polyclonal antibodies. The adiponectin levels (ug/ml) are plotted against the levels of fasting blood glucose (mg/dL). Individuals with normal fasting glucose levels—diamond, IGT—square, IFG—triangles, IGT+IFG—cross, and diabetic—asterisk. A significant correlation is apparent, especially with the globular and N-terminal antibodies.
Figure 22B:
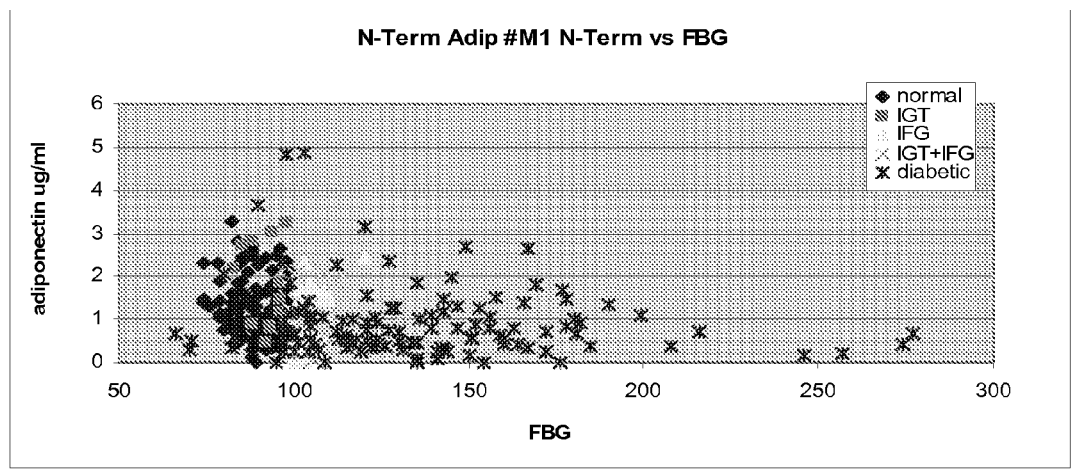
Figure 22C:
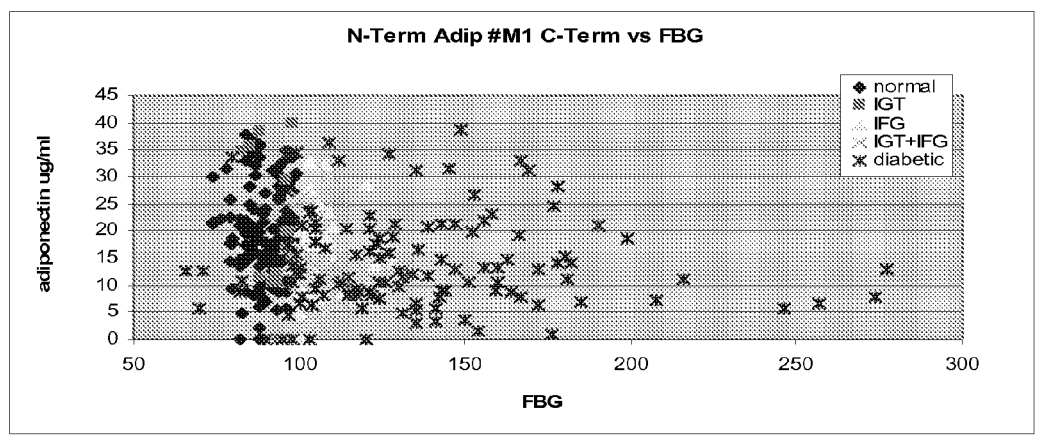
Figure 23A:
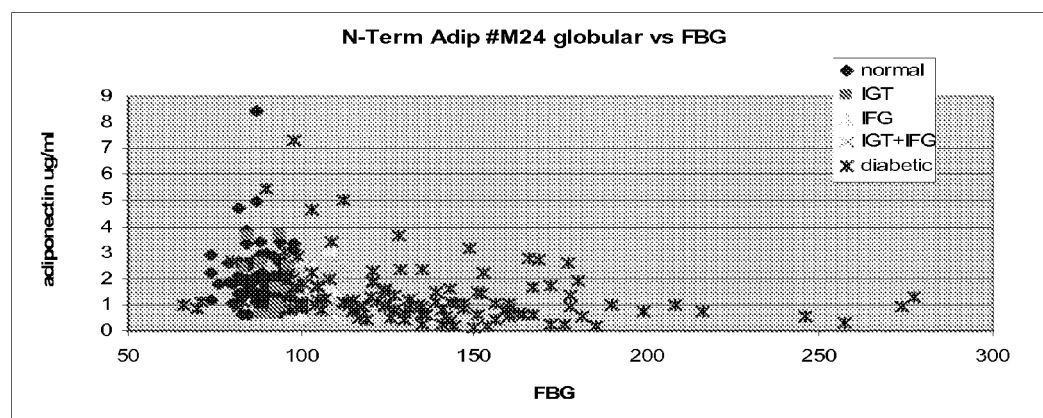
FIG. 23: Analysis of human plasma samples for adiponectin levels using mAb adiponectin M24 with globular, N-terminal and C-terminal adiponectin polyclonal antibodies. Human fasting plasma samples collected from normal, diabetic, impaired glucose tolerant (IGT), impaired fasting glucose (IFG) and both IGT & IFG individuals was assayed for levels of adiponectin. The antibody pairs for assaying were mAb adiponectin M24 in combination with globular adiponectin (FIG. 23a), N-terminal (FIG. 23b) or C-terminal (FIG. 23c) adiponectin polyclonal antibodies. The adiponectin levels (ug/ml) are plotted against the levels of fasting blood glucose (mg/dL). Individuals with normal fasting glucose levels—diamond, IGT—square, IFG—triangles, IGT+IFG—cross, and diabetic—asterisk. A significant correlation is apparent, especially with the globular and N-terminal antibodies.
Figure 23B:
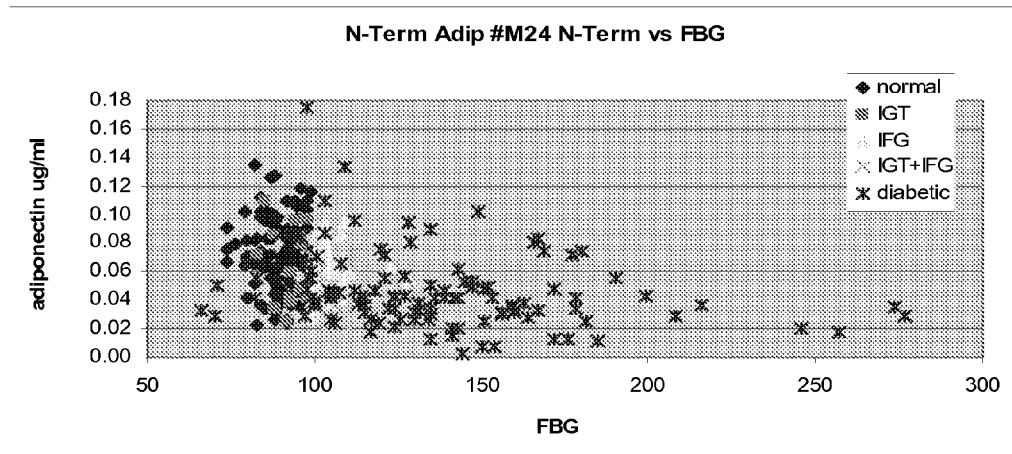
Figure 23C:
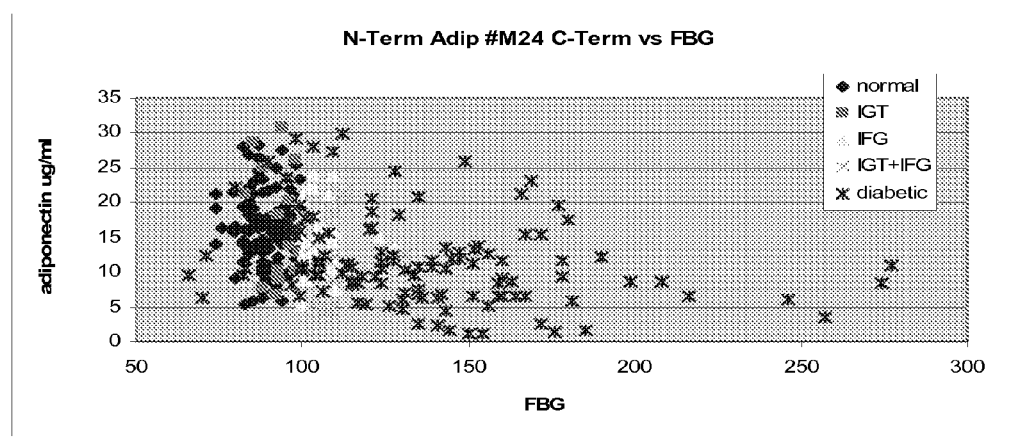
Figure 24:
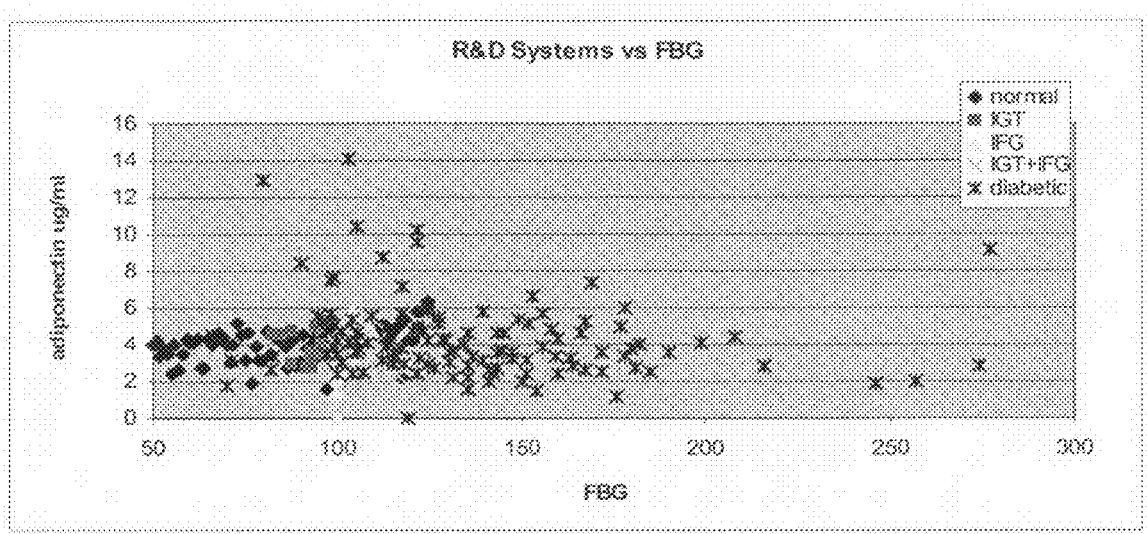
FIG. 24: Analysis of human plasma samples for adiponectin levels using the R & D adiponectin ELISA. Human fasting plasma samples collected from normal diabetic, impaired glucose tolerant (IGT), impaired fasting glucose (IFG) and both IGT & IFG individuals was assayed for levels of adiponectin. The R & D adiponectin ELISA assay was used to determin the levels of adiponectin. The adiponectin levels (ug/ml) are plotted against the levels of fasting blood glucose (mg/dL). Individuals with normal fasting glucose levels—blue diamond, IGT—pink square, IFG—yellow triangles, IGT+IFG—light blue cross, and diabetic—blue asterisk. No significant correlation is apparent.

The basic format of the assay involved immobilizing a specific anti-adiponectin monoclonal antibody on a 96 well plate (FIGS. 4 & 5). The different anti-adiponectin monoclonal antibodies used in the studies included A12820, MAB3604, MAB10651, M1 and M24. The second component of the ELISA assay was a polyclonal antibody that was directed to adiponectin. There were three different polyclonal antibodies that were used. These included N-term, C-term and globular polyclonal antibodies. These three polyclonal antibodies recognize different adiponectin domains. A schematic diagram of the different steps in the Adiponectin ELISA assays is presented in FIG. 6. It is possible to configure additional assays, using different monoclonal antibodies or polyclonal antibodies that are directed to different domains of adiponectin. Such combinations of antibodies, might provide additional assay formats that have discriminatory properties for various adiponectin isoforms that are correlated with disease states.

The different assay formats were standardized using different recombinant adiponectin proteins, which were obtained from commercial sources (FIGS. 7-12). Thus the absolute levels of adiponectin that are reported are based on the quantitation relative to the standards which were used for each assay.

Not all assays are able to detect unique adiponectin isoforms. So for each mAb in combination with each of the three polyclonal antibodies, all of the ELISA assays were not able to measure adiponectin, be it a standard adiponectin or adiponectin in human plasma. In some cases only two of the polyclonal antibodies in combination with a monoclonal antibody are useful to measure adiponectin levels. For other monoclonal antibodies, all three combinations of polyclonal antibodies are able to detect adiponectin. We have also observed that the levels of adiponectin isoform detected by the antibody combination, can vary significantly between the assays. For some, adiponectin levels of about 0.05 ug/ml (M24—N-terminus pAb), while for others, levels of about 15 ug/ml can be detected (M24—C-terminus pAb), and others have levels as high as about 60 ug/ml (A12820—globular pAb).

Characterization of Adiponectin Isoforms Recognized by Different Assays

Once the different assays were established, we noticed that different assays were able to recognize different levels of adiponectin. We then sought to determine the nature of the differences between the assays. Since adiponectin has been reported to exist in several different molecular forms we sought to determine whether the assays could recognize different adiponectin molecular forms (reviewed in Berg et al, Trends Endocrinol Metab. 2002 March; 13(2):84-9.; Trujillo and Scherer, J Intern Med. 2005 February; 257(2):167-75). Velocity gradient sedimentation provides a simple means of separating molecules on the basis of size. The separation of adiponectin via velocity sedimentation has been reported (Pajvani U B et al (2003). J. Biol. Chem. 278:9073-9085). There are additional ways of separating molecules on the basis of size, such as gel filtration chromatography which could also be used for this purpose.

Human plasma samples were separated by velocity sedimentation as outlined, and the fractions were collected. To determine the distribution of adiponectin, aliquots of the fractions were measured by ELISA, using the different assay formats. The amount of adiponectin in each fraction was determined by the different assay formats, and then plotted relative to fraction number from the velocity gradient fractionation. The data are presented in FIGS. 13-18. The observed patterns indicate that adiponectin levels vary from assay to assay. MAB3604 in combination with globular or N-terminus pAbs, primarily recognizes only smaller molecular weight adiponectin isoforms, present in fractions 3-7 (FIG. 13). On the other hand, MAB10651 in combination with all three pAbs, primarily recognizes a larger molecular weight adiponectin isoform, present in fractions 10-16 (FIG. 15). The amount of adiponectin determined by the assays varies, with MAB10651 in combination with the globular pAb measuring the highest levels, while the MAB10651 in combination with N-terminus pAb, measures the smallest amount of adiponectin. Thus, these three different assays can detect primarily a larger adiponectin isoform, however the levels of adiponectin protein detected varies, suggesting some differences in the adiponectin molecules recognized by the different combinations of antibodies.

When fractionated human plasma samples were assayed for adiponectin using mAb A12820 in combination with the three different polyclonal antibodies a very different pattern was observed (FIG. 14). Adiponectin levels were found in a number of different fractions, with a peak in fraction 5 corresponding to smaller molecular weight adiponectin. There was also a broad peak of adiponectin protein, from fraction 7-17, having a peak around fraction 13. A similar pattern was observed for all three assays, but the levels of adiponectin detected by each assay were different (FIG. 14). Thus, these three different assays can detect different adiponectin isoforms, and the levels of adiponectin protein detected varies by the assay, suggesting some differences in the adiponectin molecules recognized by the different combinations of antibodies.

When fractionated human plasma samples were assayed for adiponectin using mAb adiponectin M1 in combination with the three different polyclonal antibodies a very different pattern was observed (FIG. 16). mAb Adiponectin M1 in combination with C-terminus pAb yielded the highest levels of adiponectin. The adiponectin recognized by this form was widely distributed, in fractions 3-20. Detectable levels of adiponectin were also observed for mAbs adiponectin M1 in combination with globular and N-terminus pAbs. The levels were much lower, and appeared to be distributed over a number of different fractions.

When fractionated human plasma samples were assayed for adiponectin using mAb adiponectin M24 in combination with the three different polyclonal antibodies a very different pattern was observed (FIG. 17). mAb Adiponectin M24 in combination with C-terminus pAb yielded the highest levels of adiponectin. The adiponectin recognized by this form was widely distributed, in fractions 3-20. Barely detectable levels of adiponectin were also observed for mAbs adiponectin M24 in combination with globular and N-terminus pAbs. The levels were much lower, and appeared to be distributed over a number of different fractions.

Fractionated human plasma samples were assayed for adiponectin using the adiponectin R&D assay (FIG. 18). Adiponectin was found to be distributed in fractions 3-20, with two peaks, one at fraction 5, and the second more abundant peak in fraction 13. The pattern observed was different from the other adiponectin assays.

The velocity sedimentation results clearly demonstrate that different combinations of monoclonal and polyclonal antibodies, recognize different molecular weight forms of adiponectin. Not only are the sizes of the adiponectin, as determined by velocity sedimentation different, but the levels of adiponectin detected are also very different. Therefore, the different antibody combinations represent different assay formats that specifically recognize different adiponectin molecular forms (isoforms). The availability of these assay formats provides the opportunity to assess whether the adiponectin isoforms correlate with different physiologic or disease states.

Screening of Normal and Diabetic Plasma Samples

The levels of each of the adiponectin isoforms was determined for a population of individuals consisting of normals, diabetics, impaired glucose tolerant, and impaired fasting glucose. Fasting plasma samples were collected and stored at −80 C prior to use. Sample aliquots were then tested to determine the levels of the various adiponectin isoforms. The levels of adiponectin determined by the different ELISA assay formats was plotted against the fasting blood glucose levels, and is presented in FIGS. 19-24. The distribution of the adiponectin levels relative to fasting blood glucose levels varies between the different assays. The statistical analysis is presented below (summarized in Table 1). Some of the adiponectin assays do not show any discrimination between adiponectin levels and fasting blood glucose. These assays include the commercial adiponectin R&D assay (FIG. 24), the MAb 3604 assays (FIG. 19), and the MAB 10651 assays (FIG. 21) (summarized in Table 1). In contrast, the adiponectin assays using adiponectin mAb M1 (FIG. 22), adiponectin mAb M24 (FIG. 23), and mAb 12820 (FIG. 20) demonstrate significant correlations of the adiponectin levels to fasting glucose values (summarized in Table 1).

Statistical Analysis of Results

The ability of the various adiponectin forms to distinguish controls from Type II diabetics was examined with logistic regression models using the logistic procedure of SAS 9.1 (SAS Institute, Carey, N.C.). Separate models were run for each of the adiponectin forms. In each model group status (i.e. control or diabetic) served as the outcome variable and predictor variables included one of the adiponectin forms. Age, body mass index (BMI) and insulin served as covariates in each model. Sensitivity and specificity for the adiponectin forms were calculated using the freq and logistic procedures of SAS 9.1 Receiver operator characteristic (ROC) plots were calculated to show the variability of sensitivity and specificity for various cutoff points of adiponectin concentration for the three polyclonal forms. The area under the curve (AUC) is provided as a summary statistic for each ROC curve. The AUC can be interpreted as the probability that true case (i.e. Type II diabetic) will be correctly identified from a normal patient. For example, an AUC of 1.0 would represent a perfect test with no mis-classification whereas assays with AUC's of less than 0.5 would do no better than random assignment. Assays with ROC plots of the AUC of 0.65 and higher, with ROC plots of the AUC of 0.70 and higher being more preferred, demonstrate significant correlation and predictive value as an indicator for the predisposition to the disease state investigated, such as for example diabetes (Type II). The results for all of the different assays are summarized in Table 1.

Prior to analysis the data were screened for normality and the presence of outliers. The data conformed to assumptions of normality therefore no transformations were applied. The Grubb's test was used to test for the presence of outliers and data points determined to be significant outliers at $p<0.05$ were removed prior to the analysis. The population sample characteristics are the following: N=126 Type II diabetics (T2D) and N=124 normals were examined. The diagnostic criteria used for T2D in this sample was fasting blood glucose (FBG)>126.

The logistic regression results for the Ml globular form shows that the globular form was a significant predictor of group status (Wald Chi-Square=7.26; $p<0.01$). The odds ratio for the globular form (OR=0.84, 95% c.i. 0.74-0.95) was significantly less than 1, indicating that low levels of the Ml globular form are associated with Type II diabetes risk (FIG.

Figure 25A:
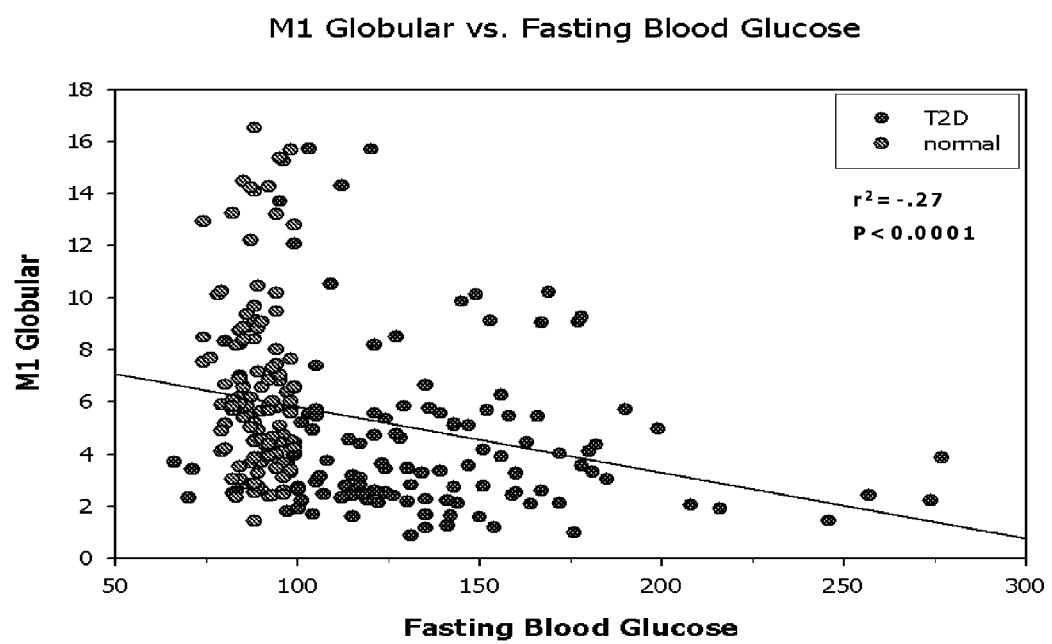
FIG. 25: Correlation of M1 Globular Form and Fasting Blood Glucose (FIG. 25a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the M1 globular form. The odds ratio for the globular form (OR=0.84, 95% c.i. 0.74-0.95) was significantly less than 1, indicating that low levels of the M1 globular form are associated with Type II diabetes risk. The ROC curve (FIG. 25b) shows the sensitivity and specificity for globular concentration cutoff values of 3.0, 4.0, and 5.0 g/ml. FP stands for false positives. The area under the curve for the M1 globular form was 0.731.
Figure 25B:
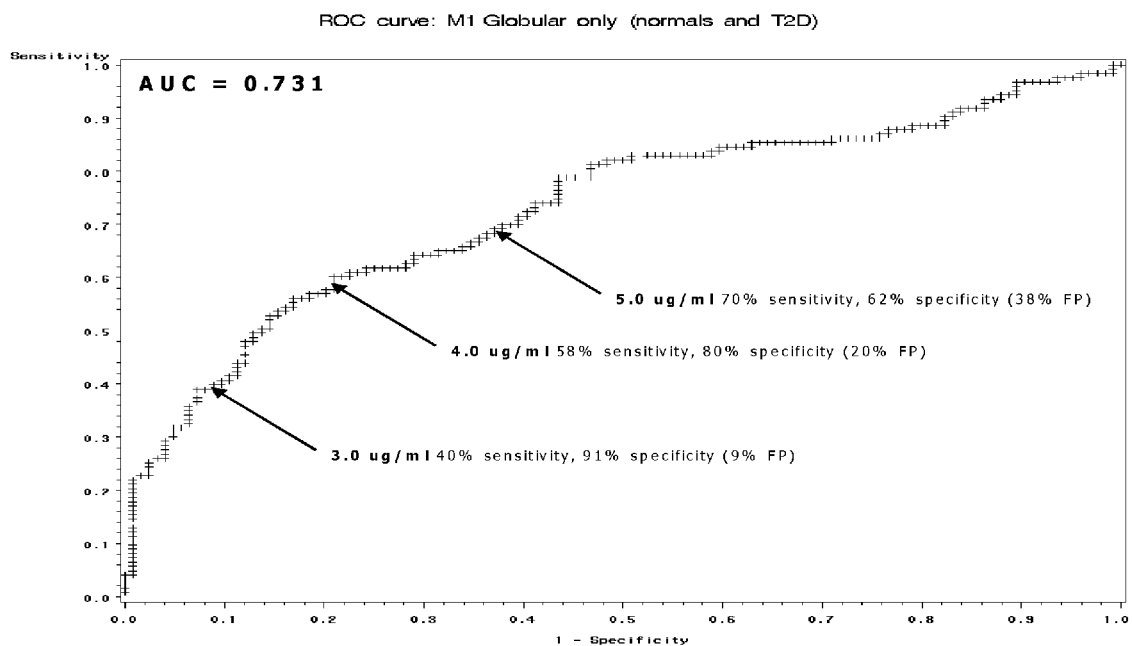

25). The ROC curve in FIG. 25 shows the sensitivity and specificity for globular concentration cutoff values of 3.0, 4.0, and 5.0 µg/ml. The area under the curve for the M1 globular form was 0.731.

Figure 26A:
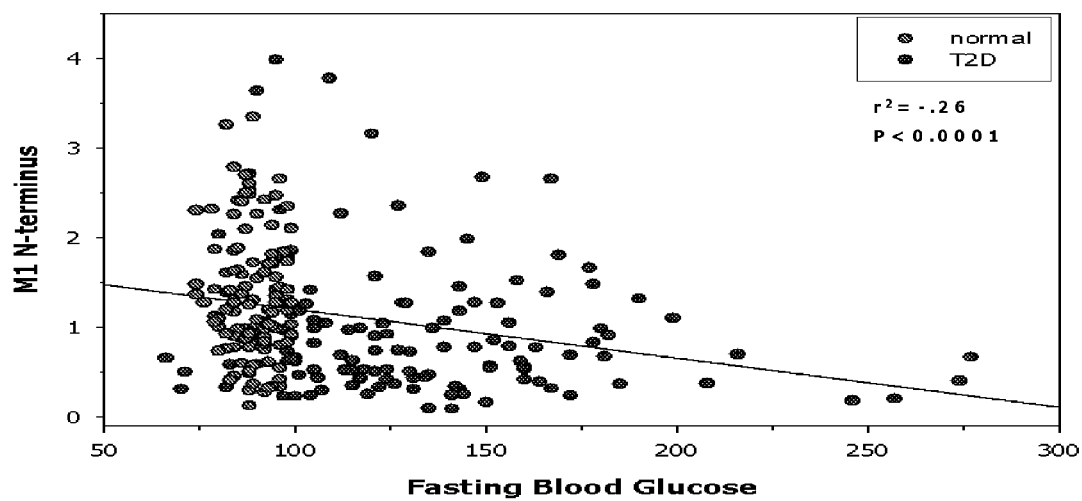
FIG. 26: Correlation of M1 N-terminus Form and Fasting Blood Glucose (FIG. 26a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the M1 N-terminus form. The odds ratio for the globular form (OR=0.53, 95% c.i. 0.32-0.88) was significantly less than 1, indicating that low levels of the M1 N-terminal form are associated with Type II diabetes risk. The ROC curve shows the sensitivity and specificity for globular concentration cutoff values of 3.0, 4.0, and 5.0 g/ml. The area under the curve (FIG. 26b) for the M1 N-terminus form was 0.705.
Figure 26B:
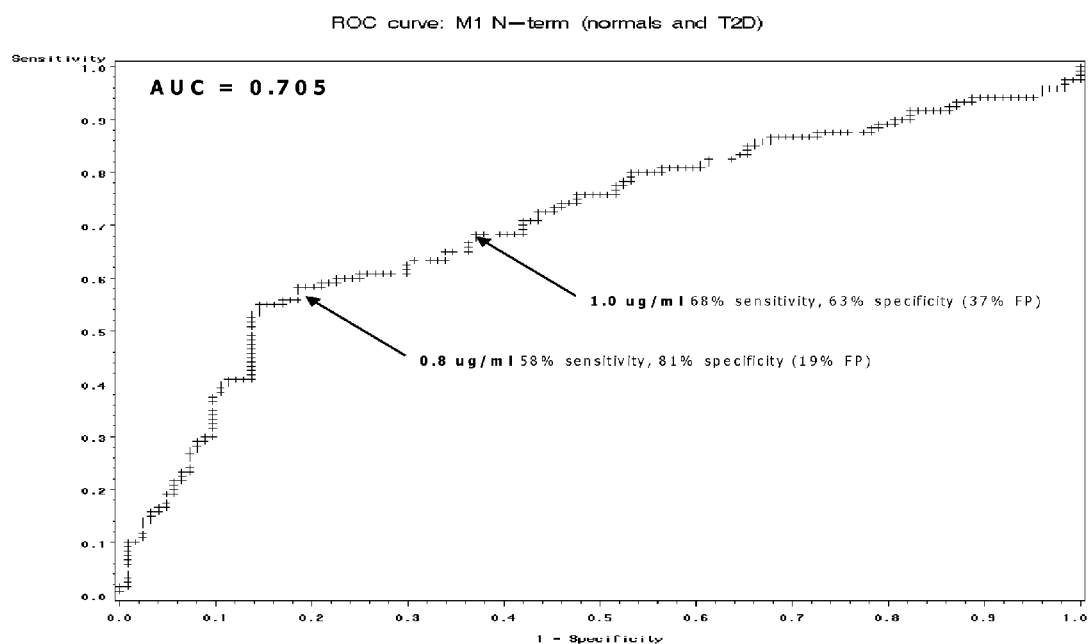

The logistic regression results for the M1 N-terminus form shows that the N-terminus form was a significant predictor of group status (Wald Chi-Square=6.01; p<0.01). The odds ratio for the globular form (OR=0.53, 95% c.i. 0.32-0.88) was significantly less than 1, indicating that low levels of the M1 N-terminus form are associated with Type II diabetes risk (FIG. 26). The ROC curve in FIG. 26 shows the sensitivity and specificity for N-terminus concentration cutoff values of 0.8 and 1.0 µg/ml. The area under the curve for the N-terminus form was 0.705.

Figure 27A:
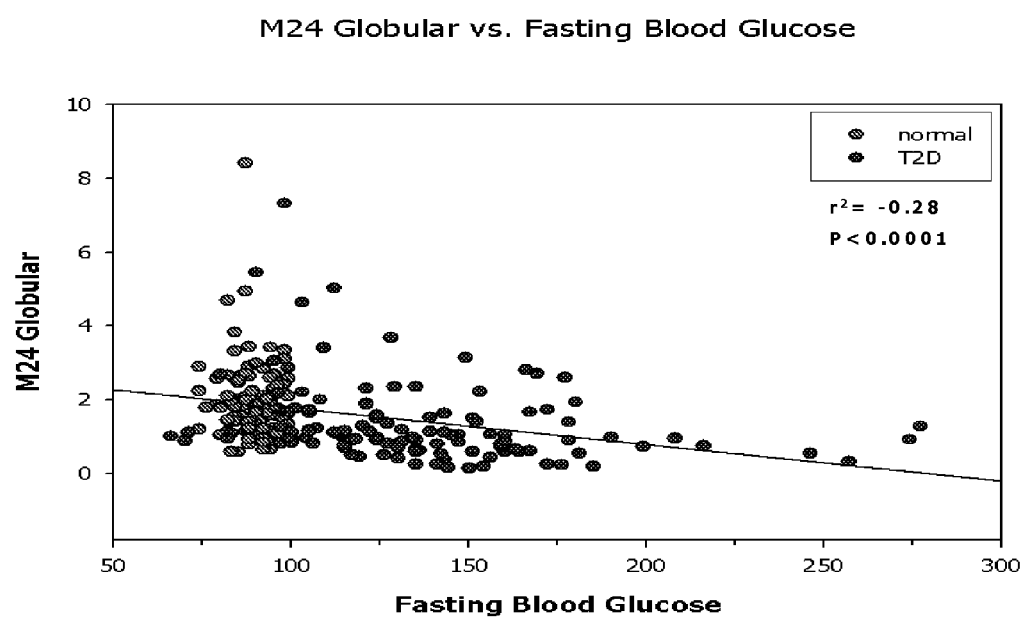
FIG. 27: Correlation of M24 Globular Form and Fasting Blood Glucose (FIG. 27a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the M24 globular form. The odds ratio for the globular form (OR=0.47, 95% c.i. 0.30-0.72) was significantly less than 1, indicating that low levels of the M24 globular form are associated with Type II diabetes risk. The ROC curve shows the sensitivity and specificity for globular concentration cutoff values of 3.0, 4.0, and 5.0 g/ml. The area under the curve (FIG. 27b) for the M24 globular form was 0.742.
Figure 27B:
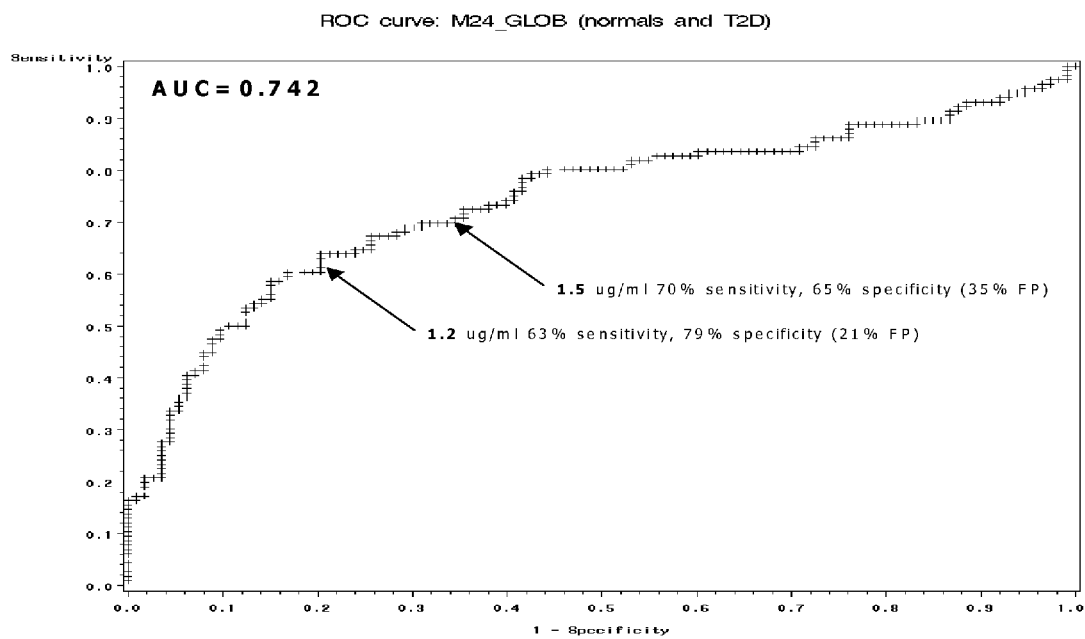

The logistic regression results for the M24 globular form shows that the globular form was a significant predictor of group status (Wald Chi-Square=11.9; p<0.0005). The odds ratio for the globular form (OR=0.47, 95% c.i. 0.30-0.72) was significantly less than 1, indicating that low levels of the M24 globular form are associated with Type II diabetes risk (FIG. 27). The ROC curve in FIG. 27 shows the sensitivity and specificity for globular concentration cutoff values of 1.2 and 1.5 µg/ml. The area under the curve for the M1 globular form was 0.742.

Figure 28A:
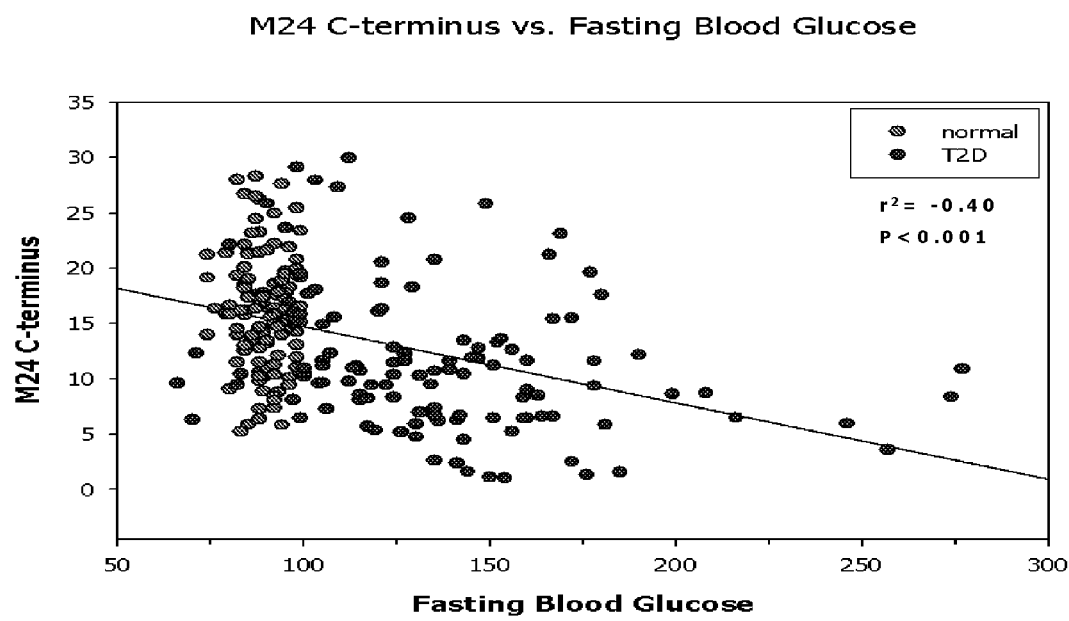
FIG. 28: Correlation of M24 C-terminus Form and Fasting Blood Glucose (FIG. 28a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the M24 C-terminus form. The odds ratio for the C-terminus form (OR=0.87, 95% c.i. 0.80-0.92) was significantly less than 1, indicating that low levels of the M24 C-terminus form are associated with Type II diabetes risk. The ROC curve shows the sensitivity and specificity for globular concentration cutoff values of 3.0, 4.0, and 5.0 g/ml. The area under the curve (FIG. 28b) for the M24 C-terminus form was 0.740.
Figure 28B:
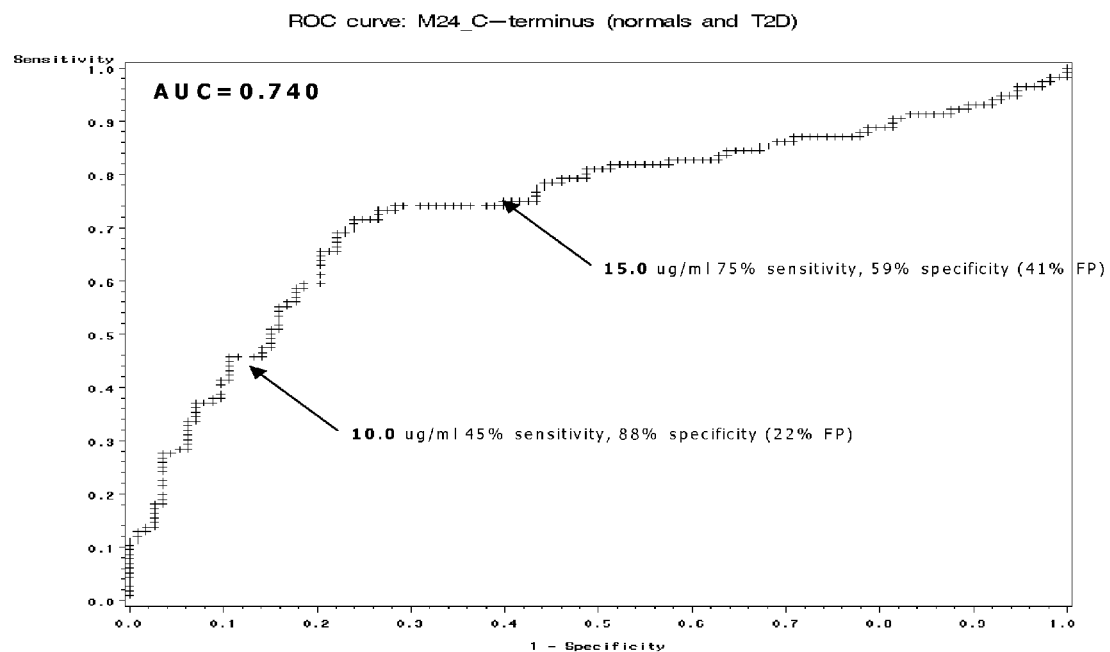

The logistic regression results for the M24 C-terminus form shows that the C-terminus form was a significant predictor of group status (Wald Chi-Square=15.9; p<0.0001). The odds ratio for the C-terminus form (OR=0.87, 95% c.i. 0.80-0.92) was significantly less than 1, indicating that low levels of the M24 C-terminus form are associated with Type II diabetes risk (FIG. 28). The ROC curve in FIG. 28 shows the sensitivity and specificity for C-terminus concentration cutoff values of 10.0 and 15.0 µg/ml. The area under the curve for the M24 C-terminus form was 0.740.

Figure 29A:
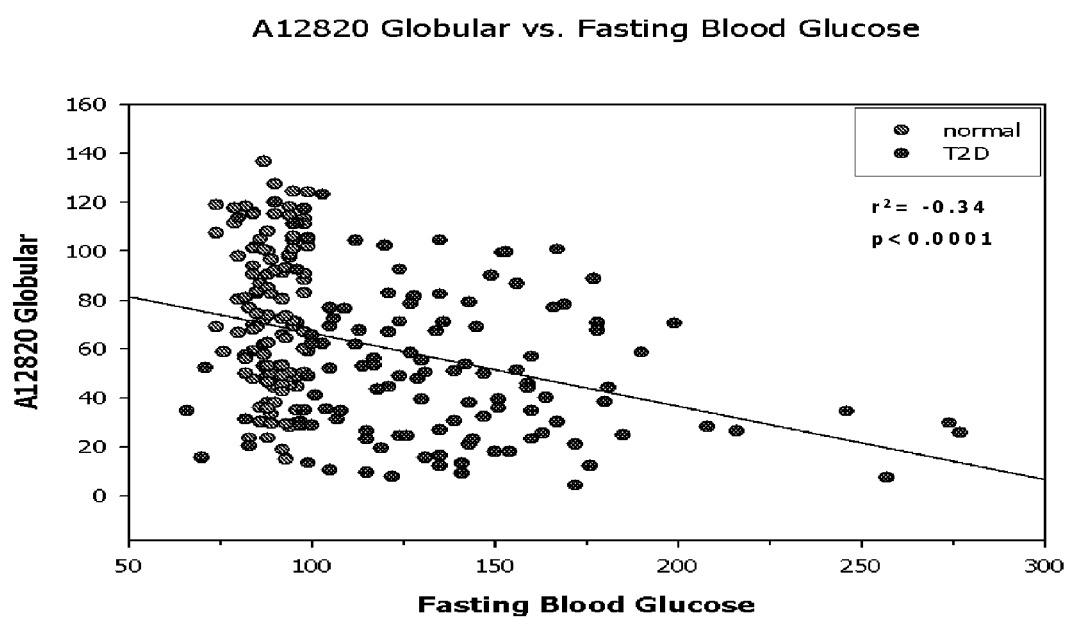
FIG. 29: Correlation of A12820 Globular Form and Fasting Blood Glucose (FIG. 29a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the A12820 globular form. The odds ratio for the A12820 globular form (OR=0.87, 95% c.i. 0.80-0.92) was significantly less than 1, indicating that low levels of the A12820 globular form are associated with Type II diabetes risk. The ROC curve shows the sensitivity and specificity for globular concentration cutoff values of 3.0, 4.0, and 5.0 g/ml. The area under the curve (FIG. 29b) for the A12820 globular form was 0.714.
Figure 29B:
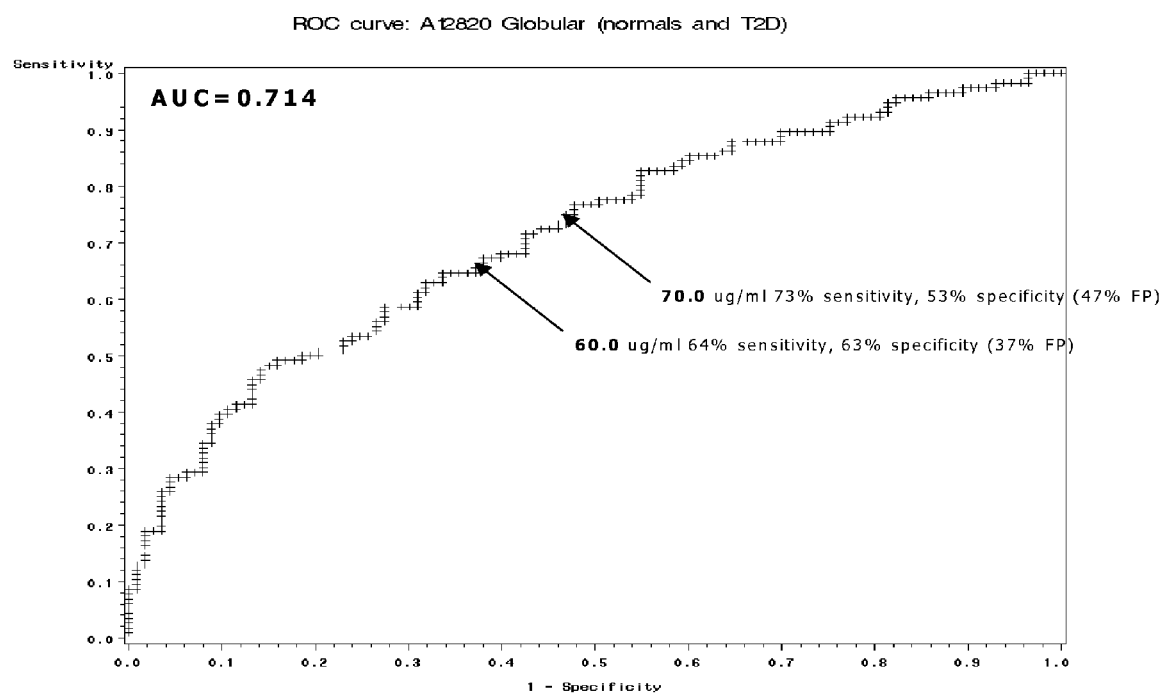

The logistic regression results for the A12820 globular form shows that the A12820 globular form was a significant predictor of group status (Wald Chi-Square=15.9; p<0.0001). The odds ratio for the A12820 globular form (OR=0.87, 95% c.i. 0.80-0.92) was significantly less than 1, indicating that low levels are associated with Type II diabetes risk (FIG. 29). The ROC curve in FIG. 29 shows the sensitivity and specificity for A12820 Globular Form concentration cutoff values of 3.0, 4.0, and 5.0 µg/ml. The area under the curve for the M1 globular form was 0.714.

Figure 30A:
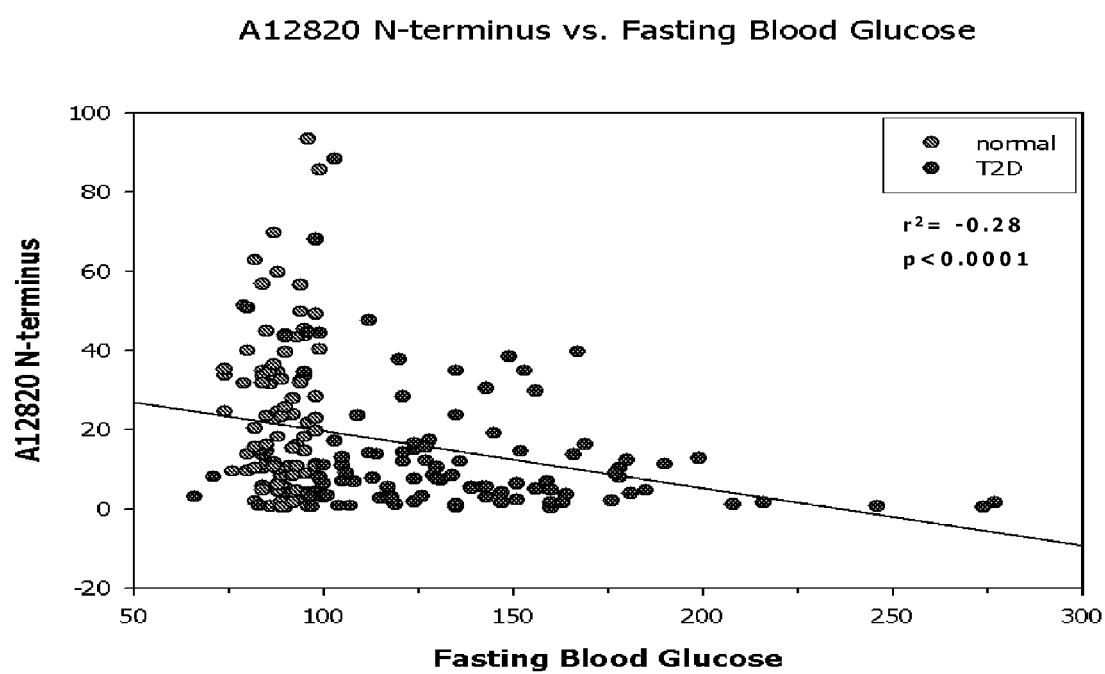
FIG. 30: Correlation of A12820 N-terminus Form and Fasting Blood Glucose (FIG. 30a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the A12820 N-terminus form. The odds ratio for the A12820 N-terminus form (OR=0.97, 95% c.i. 0.95-0.99) was significantly less than 1, indicating that low levels of the A12820 N-terminus form are associated with Type II diabetes risk. The ROC curve shows the sensitivity and specificity for globular concentration cutoff values of 3.0, 4.0, and 5.0 g/ml. The area under the curve (FIG. 30b) for the A12820 N-terminus form was 0.673.
Figure 30B:
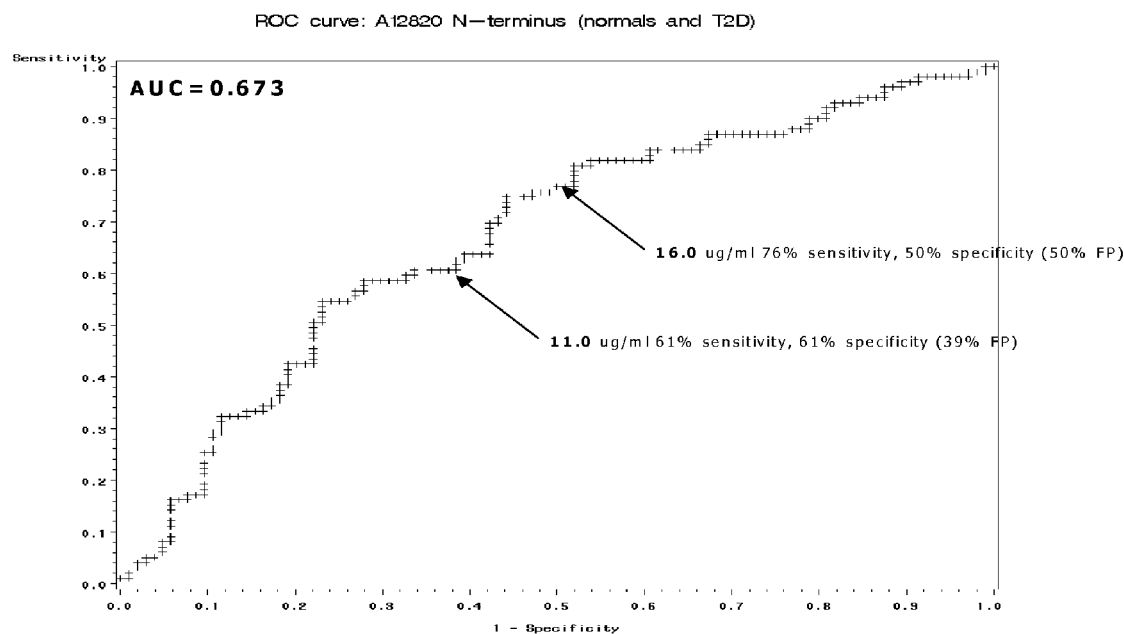

The logistic regression results for the A12820 N-terminus form shows that the A12820 N-terminus form was a significant predictor of group status (Wald Chi-Square=5.18; p=0.02). The odds ratio for the A12820 N-terminus form (OR=0.97, 95% c.i. 0.95-0.99) was significantly less than 1, indicating that low levels are associated with Type II diabetes risk. (FIG. 30). The ROC curve in FIG. 30 shows the sensitivity and specificity for A12820 N-terminus Form concentration cutoff values of 11.0 and 16.0 µg/ml. The area under the curve for the M1 N-terminus form was 0.673.

Figure 31A:
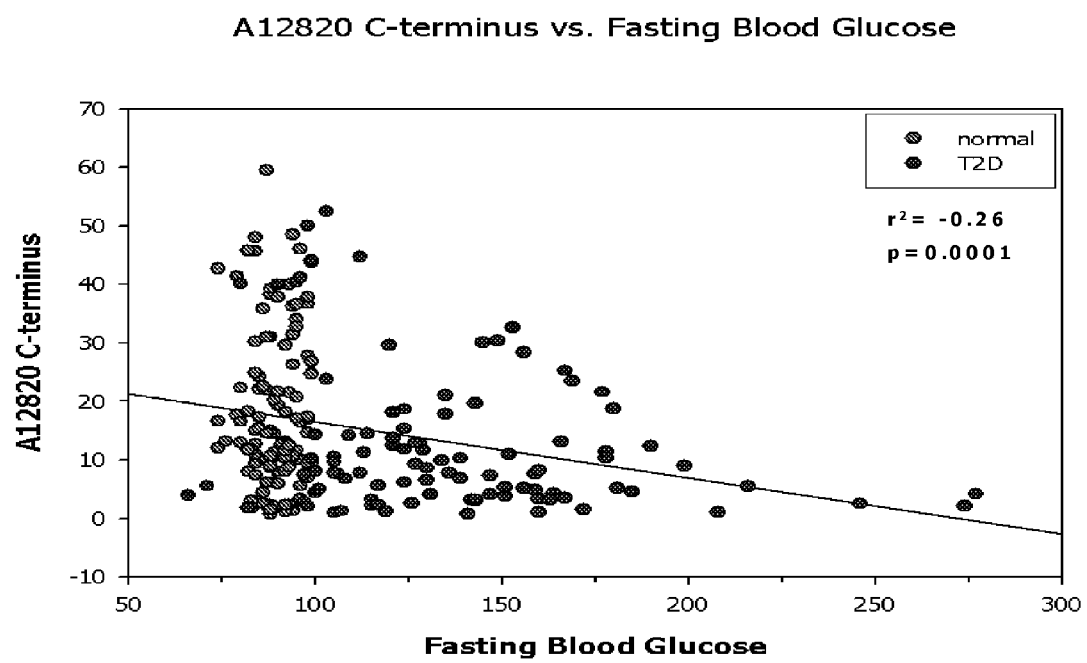
FIG. 31: Correlation of A12820 C-terminus Form and Fasting Blood Glucose (FIG. 31a). Sample Characteristics: N=126 Type II diabetics (T2D) and N=124 normals were examined. The diagnostic criteria used for T2D in this sample was fasting blood glucose (FBG)>126. The level of adiponectin is in ug/ml, and is the A12820 C-terminus form. The odds ratio for the A12820 C-terminus form (OR=0.97, 95% c.i. 0.93-0.99) was significantly less than 1, indicating that low levels of the A12820 C-terminus form are associated with Type II diabetes risk. The ROC curve shows the sensitivity and specificity for globular concentration cutoff values of 3.0, 4.0, and 5.0 g/ml. The area under the curve (FIG. 31b) for the A12820 C-terminus form was 0.663.
Figure 31B:
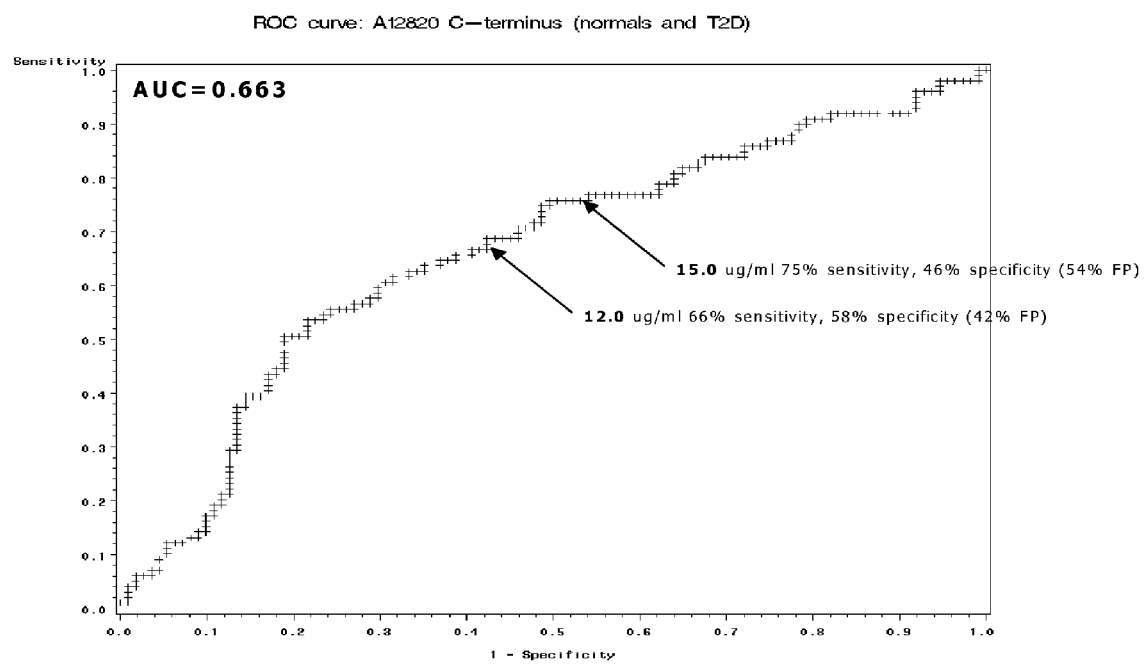

The logistic regression results for the A12820 C-terminus form. The A12820 C-terminus form was a significant predictor of group status (Wald Chi-Square=4.91; p=0.03). The odds ratio for the A12820 C-terminus form (OR=0.97, 95% c.i. 0.93-0.99) was significantly less than 1, indicating that low levels are associated with Type II diabetes risk (FIG. 31). The ROC curve in FIG. 31 shows the sensitivity and specificity for A12820 C-terminus Form concentration cutoff values of 12.0 and 15.0 µg/ml. The area under the curve for the M1 globular form was 0.663.

The statistical analysis of the remaining assays is summarized in Table 1. These do not appear to show significance from the analysis which was performed.

Sequence Determination of the CDRs of the Hybridoma Cell Lines M1 & M24.

The sequence of the CDRs of mAb adiponectin M1 and M24 IgG cDNA was determined and is shown in FIGS. 32 and 33. The sequence of the two IgGs is very similar, yet different. Both of these IgG proteins bind to the N-terminal adiponectin region, encompassing amino acids 19-34, ETTQGPGVLLPLPKGAC (SEQ ID NO. 3).

Discussion

ELISA Assays that Recognize Adiponectin

ELISA assays recognizing adiponectin were developed. Different monoclonal antibodies were used as capture antibodies, in combination with three different polyclonal antibodies. In most cases, the antibody combinations were able to recognize adiponectin, while some combinations were not able to detect adiponectin (MAB 3604 C-terminus). All of the assays could be standardized by using recombinant forms of adiponectin. The standardization provided a basis for determining the levels of adiponectin that are found in biological samples such as plasma. The ELISA assays could then be used to measure adiponectin levels, to determine the size distribution of the adiponectin molecular forms, and to determine whether the concentration of specific adiponectin isoforms correlated to a specific physiologic status. It is important to note that the assays of the invention do not require any sample pretreatment, or denaturation, of samples prior to measurement. As such, the assays measure native forms of adiponectin.

Different Adiponectin Molecular Forms

To demonstrate that different adiponectin molecular forms are being recognized by the various ELISA assays, human plasma was fractionated by velocity sedimentation, and the fractions were assayed for adiponectin levels using the different ELISA assays. FIGS. 13-18, clearly demonstrate that the distribution of adiponectin levels is significantly different depending on the combination of polyclonal and monoclonal antibodies that are used. For some of the assays, only a low molecular weight adiponectin form is recognized (FIG. 13, fractions 4, 5 6). For other assays, only a higher molecular weight form of adiponectin is recognized (FIG. 15, fractions 11-14). Finally, some of the assays recognize both higher and lower molecular weight forms of adiponectin (FIGS. 14, 16, 17). Not only do the assays recognize different sizes of adiponectin as demonstrated by the velcosity sedimentation profiles (FIGS. 13-18), but some of the assays (FIGS. 14, 15, 16, 17) recognize different levels of adiponectin, again suggesting that there are unique differences in the types of adiponectin molecules which are being recognized by the different assays. The fact that the assays recognize different adiponectin molecular weight forms, provides a powerful simple tool to assess the differences in adiponectin between individuals, and to determine whether any of the adiponectin forms correlates to disease status.

Levels of Adiponectin Forms Vary Between Individuals

When different assays were used to determine the levels of adiponectin in different individuals, there were significant differences in the levels of adiponectin that were observed. For some of the assays, the levels of adiponectin differ by 10-50 fold. These results suggest, that some adiponectin assays can measure most of the adiponectin isoforms that are present in human plasma or serum, while other assays measure a very specific adiponectin isoform(s) For example, mAb 12820 in combination with the globular domain pAb, detects from 30-120 ug/ml of adiponectin. In contrast, mAb adiponectin M24 in combination with N-terminus polyclonal antibody detects only 0.02-0.1 ug/ml. The difference represents about a 1000 fold difference in the levels of adiponectin which are detected in human plasma. These differences are apparent in FIGS. 13-18, where the adiponectin levels are determined in fractionated human plasma. These differences are also observed in FIGS. 19-24, Some of these differences are significant in terms of correlation to phenotype (summarized in Table 1) while others are not. The ability to characterize plasma samples from a wide variety of disease states will provide the correlations that are significant.

Certain Adiponectin Forms Correlate to Glucose Levels

All of the different adiponectin assays were used to screen human plasma sample collections to look for correlations to glucose. We observed, that certain adiponectin isoforms show moderate strength correlations to glucose. The assays which show significant correlations to glucose are the mAb adiponectin M1 globular and N-terminus (FIGS. 22, 25, 26), the mAb adiponectin M24 globular and C-terminus (FIGS. 23, 27, 28) the mAb A12820 globular, N-terminus and C-terminus (FIGS. 20, 29, 30, 31), and MAB1051 N-terminus and C-terminus (summarized in Table 1). None of the other assays, including the R&D commercial adiponectin assay, demonstrate any significant association to glucose.

Certain Adiponectin Forms are Predictive of the Diabetic State

Low adiponectin levels of the mAb adiponectin M1 globular and N-terminus (FIGS. 25, 26), the mAb adiponectin M24 globular and C-terminus (FIGS. 27, 28), and mAb 12820 globular (FIG. 29), are significant predictors of diabetes (summarized in Table 1). This observation suggests that these assays will be of interest to ascertain which normal individuals will become diabetic, which individuals have the best response to a specific diabetes treatment, and which individuals will have the best prognosis for their diabetes. The ROC plots show that the specific forms have good levels of specificity and sensitivity for utility in the clinic. Specifically, levels of sensitivity/specificity of 60% or greater can be useful in the clinic. The ability to use these assays for further predictive value depends on collecting longitudinal samples, to determine the correlation to disease progression and to treatment outcomes.

The above examples illustrating the monoclonal and polyclonal antibodies of the invention, the Elisa methods of the invention and the predicative/diagnostic methods of adiponectin forms/levels to certain disease states such as diabetes, are not meant to limit the scope of the invention. These examples are included for purposes of illustration and the present invention is limited only by the scope of the claims herein.

TABLE 1

| | Regression Model | | | Correlation of Fasting Blood Glucose and Adiponectin Form | |
|---|---|---|---|---|---|
| | Wald | | | | |
| Adiponectin Form | Chi-Square | p-value | ROC AUC | r2 | p-value |
| M1 Globular form | 7.26 | 0.0100 | 0.73 | −0.27 | 0.0001 |
| M1 N-terminus form | 6.01 | 0.0100 | 0.70 | −0.26 | 0.0001 |
| M1 C-terminus form | 3.23 | 0.0700 | 0.66 | −0.25 | 0.0001 |
| M24 Globular form | 11.97 | 0.0005 | 0.74 | −0.28 | 0.0001 |
| M24 N-terminus form | 22.38 | 0.0001 | 0.78 | −0.43 | 0.0001 |
| M24 C-terminus form | 15.99 | 0.0001 | 0.74 | −0.40 | 0.0001 |
| A12820 Globular form | 11.91 | 0.0006 | 0.71 | −0.34 | 0.0001 |
| A12820 N-terminus form | 5.18 | 0.0228 | 0.67 | −0.28 | 0.0001 |
| A12820 C-terminus form | 4.91 | 0.0267 | 0.66 | −0.26 | 0.0001 |
| MAB1051 Globular form | 0.49 | 0.4851 | 0.58 | −0.10 | 0.1100 |
| MAB1051 N-terminus form | 1.77 | 0.1828 | 6.64 | −0.22 | 0.0007 |
| MAB1051 C-terminus form | 0.40 | 0.5272 | 0.66 | −0.19 | 0.0030 |
| MAB3604 Globular form | 0.00 | 0.9895 | 0.47 | −0.08 | 0.1900 |
| MAB3604 N-terminus form | 1.50 | 0.2203 | 0.49 | −0.02 | 0.7900 |
| R&D form | 4.14 | 0.0419 | 0.51 | −0.05 | 0.3400 |

The invention claimed is:

1. A purified adiponectin antibody comprising SEQ ID NO:18.

2. A purified adiponectin antibody comprising SEQ ID NO:19.

* * * * *

SEQUENCE LISTING

<160> NUMBER OF SEQ ID NOS: 21

<210> SEQ ID NO 1
<211> LENGTH: 21
<212> TYPE: PRT
<213> ORGANISM: Homo sapiens

<400> SEQUENCE: 1

Glu Thr Thr Thr Gln Gly Pro Gly Val Leu Leu Pro Leu Pro Lys Gly
 1               5                  10                  15

Ala Ser Thr Gly Cys
            20

<210> SEQ ID NO 2
<211> LENGTH: 21
<212> TYPE: PRT
<213> ORGANISM: Homo sapiens

<400> SEQUENCE: 2

Cys Tyr Ala Asp Asn Val Asn Asp Ser Thr Phe Thr Gly Phe Leu Leu
 1               5                  10                  15

Tyr His Asp Thr Asn

<210> SEQ ID NO 3
<211> LENGTH: 17
<212> TYPE: PRT
<213> ORGANISM: Homo sapiens

<400> SEQUENCE: 3

Glu Thr Thr Gln Gly Pro Gly Val Leu Leu Pro Leu Pro Lys Gly Ala
 1               5                  10                  15

Cys

<210> SEQ ID NO 4
<211> LENGTH: 336
<212> TYPE: DNA
<213> ORGANISM: Homo sapiens

<400> SEQUENCE: 4
agctggtgga gatcatgggc tgatcttgtg aggccagggg ccttagtcaa gttgtcctgc      60
aaagcttctg gcttcaacat taaagacttc catatgagtt gggtgaagca gaggcctgaa    120
cagggcctgg agtggattgg atggattgat tataacatca gacacatcct ccaacacagc    180
ctacctgcag ctcagcagcc tgacatctga ggacactgcc gtctattact gtagtaggag    240
cggtcccgcc tggtttgctt actggggcca agggactctg gtcactgtct ctgcagccaa    300
aacgacaccc ccatctgtct atccactggc ccccct                              336

<210> SEQ ID NO 5
<211> LENGTH: 329
<212> TYPE: DNA
<213> ORGANISM: Homo sapiens

<400> SEQUENCE: 5
atgacccaga ctccactctc cctgcctgtc agtcttggag atcaagcctc catctcttgc      60
agatctagtc agagtattgt atatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgagg atctgggagt ttattactgc tttcaaggtt cgcatgttcg tcggacgttc    300
ggtggaggca ccaagctgga aatcagacg                                     329

<210> SEQ ID NO 6
<211> LENGTH: 383
<212> TYPE: DNA
<213> ORGANISM: Homo sapiens

<400> SEQUENCE: 6
gctggtggag atcatggggc tgaacttgtg aggccagggg ccttagtcag gttgtcctgt      60
aaagcttctg gcttcaacat taaagactac catatgtcct ggctgaagca gaggcctgaa    120
cagggcctgg agtggattgg atggattgat cctgagaatg gtaatgctat acatgacccg    180
aagttccagg acaaggccaa tataacagca gacacatcct ccaacacagc ctacctgcag    240
ctcagcagcc tgacatctga ggacactgcc gtctatttct gtgctagatc ggggcctgcc    300
tggtttgctt actggggcca agggactctg gtcactgtct ctgcagccaa aacgacaccc    360
ccatctgtct atccactggc ccc                                            383

<210> SEQ ID NO 7
<211> LENGTH: 330

```
<212> TYPE: DNA
<213> ORGANISM: Homo sapiens

<400> SEQUENCE: 7
atgacccaga ctccactctc cctgcctgtc agtcttggag atcaagcctc catctcttgc      60
agatctagtc agaccattgt atatagtaat ggaaacacct atttagaatg gtacctgcag     120
aaaccaggcc agtctccaaa gctcctgatc tacaaagttt ccaaccgatt ttctggggtc     180
ccagacaggt tcagtggcag tggatcaggg acagatttca cactcaagat cagcagagtg     240
gagtctgagg atctgggaat ttattactgc tttcaaggtt cacatgttcc tcggacgttc     300
ggtggaggca ccaagctgga aatcaaacgg                                      330

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggtgaagc tggtggagwc wgg                                              23

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggggccagtg gatagac                                                     17

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagttccga gctccagatg acccagactc ca                                    32

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttggtgcag catcagc                                                     17

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

```
caggtsmarc tgswgsagwc wgg                                          23
```

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 13

```
cgacaagtcg actagcccctt gaccaggcat cc                               32
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 14

```
gacattsagc tsacccagtc tcca                                         24
```

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 15

```
cgactagtcg actggtggga agatggatac ag                                32
```

<210> SEQ ID NO 16
<211> LENGTH: 244
<212> TYPE: PRT
<213> ORGANISM: Homo sapiens

<400> SEQUENCE: 16

Met Leu Leu Leu Gly Ala Val Leu Leu Leu Ala Leu Pro Gly His
 1               5                  10                  15

Asp Gln Glu Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe

```
                         165                 170                 175
Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 17
<211> LENGTH: 21
<212> TYPE: PRT
<213> ORGANISM: Homo sapiens

<400> SEQUENCE: 17

Cys Tyr Ala Asp Asn Asp Asn Asp Ser Thr Phe Thr Gly Phe Leu Leu
1               5                   10                  15

Tyr His Asp Thr Asn
            20

<210> SEQ ID NO 18
<211> LENGTH: 110
<212> TYPE: PRT
<213> ORGANISM: Homo sapiens

<400> SEQUENCE: 18

Met Thr Gln Thr Pro Leu Ser Leu Pro Val Ser Leu Gly Asp Gln Ala
1               5                   10                  15

Ser Ile Ser Cys Arg Ser Ser Gln Ser Ile Val Tyr Ser Asn Gly Asn
            20                  25                  30

Thr Tyr Leu Glu Trp Tyr Leu Gln Lys Pro Gly Gln Ser Pro Lys Leu
        35                  40                  45

Leu Ile Tyr Lys Val Ser Asn Arg Phe Ser Gly Val Pro Asp Arg Phe
    50                  55                  60

Ser Gly Ser Gly Ser Gly Thr Asp Phe Thr Leu Lys Ile Ser Arg Val
65                  70                  75                  80

Glu Ala Glu Asp Leu Gly Val Tyr Tyr Cys Phe Gln Gly Ser His Val
                85                  90                  95

Arg Arg Thr Phe Gly Gly Gly Thr Lys Leu Glu Ile Arg Arg
            100                 105                 110

<210> SEQ ID NO 19
<211> LENGTH: 114
<212> TYPE: PRT
<213> ORGANISM: Homo sapiens

<400> SEQUENCE: 19

Ser Trp Trp Arg Ser Trp Ala Asp Leu Val Arg Pro Gly Ala Leu Val
1               5                   10                  15

Lys Leu Ser Cys Lys Ala Ser Gly Phe Asn Ile Lys Asp Phe His Met
            20                  25                  30

Ser Trp Val Lys Gln Arg Pro Glu Gln Gly Leu Glu Trp Ile Gly Trp
        35                  40                  45

Ile Asp Pro Glu Asn Ser Asn Thr Ile Tyr Asp Pro Lys Phe Gln Gly
    50                  55                  60

Lys Ala Ile Ile Thr Ser Asp Thr Ser Ser Asn Thr Ala Tyr Leu Gln
```

```
                 65                  70                  75                  80
Leu Ser Ser Leu Thr Ser Glu Asp Thr Ala Val Tyr Tyr Cys Ser Arg
                     85                  90                  95

Ser Gly Pro Ala Trp Phe Ala Tyr Trp Gly Gln Gly Thr Leu Val Thr
                100                 105                 110

Val Ser

<210> SEQ ID NO 20
<211> LENGTH: 110
<212> TYPE: PRT
<213> ORGANISM: Homo sapiens

<400> SEQUENCE: 20

Met Thr Gln Thr Pro Leu Ser Leu Pro Val Ser Leu Gly Asp Gln Ala
 1               5                  10                  15

Ser Ile Ser Cys Arg Ser Ser Gln Thr Ile Val Tyr Ser Asn Gly Asn
                20                  25                  30

Thr Tyr Leu Glu Trp Tyr Leu Gln Lys Pro Gly Gln Ser Pro Lys Leu
            35                  40                  45

Leu Ile Tyr Lys Val Ser Asn Arg Phe Ser Gly Val Pro Asp Arg Phe
        50                  55                  60

Ser Gly Ser Gly Ser Gly Thr Asp Phe Thr Leu Lys Ile Ser Arg Val
65                  70                  75                  80

Glu Ser Glu Asp Leu Gly Ile Tyr Tyr Cys Phe Gln Gly Ser His Val
                85                  90                  95

Pro Arg Thr Phe Gly Gly Gly Thr Lys Leu Glu Ile Lys Arg
                100                 105                 110

<210> SEQ ID NO 21
<211> LENGTH: 128
<212> TYPE: PRT
<213> ORGANISM: Homo sapiens

<400> SEQUENCE: 21

Ala Gly Gly Asp His Gly Ala Glu Leu Val Arg Pro Gly Ala Leu Val
 1               5                  10                  15

Arg Leu Ser Cys Lys Ala Ser Gly Phe Asn Ile Lys Asp Tyr His Met
                20                  25                  30

Ser Trp Leu Lys Gln Arg Pro Glu Gln Gly Leu Glu Trp Ile Gly Trp
            35                  40                  45

Ile Asp Pro Glu Asn Gly Asn Ala Ile His Asp Pro Lys Phe Gln Asp
        50                  55                  60

Lys Ala Asn Ile Thr Ala Asp Thr Ser Ser Asn Thr Ala Tyr Leu Gln
65                  70                  75                  80

Leu Ser Ser Leu Thr Ser Glu Asp Thr Ala Val Tyr Phe Cys Ala Arg
                85                  90                  95

Ser Gly Pro Ala Trp Phe Ala Tyr Trp Gly Gln Gly Thr Leu Val Thr
                100                 105                 110

Val Ser Ala Ala Lys Thr Thr Pro Pro Ser Val Tyr Pro Leu Ala Pro
            115                 120                 125
```